United States Patent [19]

Finn

[11] Patent Number: 5,225,564
[45] Date of Patent: Jul. 6, 1993

[54] 5-HETEROCYCLIC 2-(2-IMIDAZOLIN-2-YL)PYRIDINES, USEFUL AS HERBICIDAL AGENTS AND METHODS FOR THE PREPARATION THEREOF

[75] Inventor: John M. Finn, Mercerville, N.J.

[73] Assignee: American Cyanamid Company, Stamford, Conn.

[21] Appl. No.: 694,708

[22] Filed: May 2, 1991

Related U.S. Application Data

[62] Division of Ser. No. 457,606, Dec. 27, 1989, Pat. No. 5,039,333.

[51] Int. Cl.$^5$ ............... C07D 401/04; C07D 213/55; C07D 471/04
[52] U.S. Cl. ..................... 546/278; 546/280; 546/276; 546/275; 546/283; 546/284; 546/299; 546/268; 546/341; 546/116; 544/96
[58] Field of Search ............... 546/278, 280, 276, 275, 546/268, 283, 284, 299, 341, 116

[56] References Cited

U.S. PATENT DOCUMENTS 4,188,487  2/1980  Los .
4,758,667  7/1988  Szczepanski et al. ............... 546/278
4,798,619  1/1989  Los ..................... 548/301

OTHER PUBLICATIONS

F. Meskens, Synthesis, 1981, 501.
S. Sandler and W. Karo, "Organic Functional Group Preparations", vol. III, pp. 2–76, Academic Press, N.Y., 1972.
L. Fieser, J. Amer. Chem. Soc., 1954, 76, 1945.
I. Schmolka and P. Spoerri, J. Org. Chem., 1957, 22, 943.
E. Bergman, Chem. Rev., 1953, 53, 309.
D. Seebach et al., Tetrahedron, 1984, 40, 1313.
D. Seebach et al., Angew. Chem. Int. Ed., 1986, 25, 178.
D. Seebach et al., Helv. Chim. Acta., 1987, 70, 448.
D. Seebach et al., Helv. Chim. Acta., 1985, 68, 144.
D. Seebach et al., Helv Chim. Acta., 1985, 68, 135.
D. Seebach et al., Helv Chim. Acta., 1985, 68, 1243.
P. Reward and D. Seebach, Angew. Chem. Int. Ed., 1986, 25, 843.
T. Polonski, Tetrahedron, 1983, 39, 3139.
D. Seebach et al., Helv. Chim. Acta., 1986, 69, 1147.
M. Rai et al., Indian J. Chem. Sect. B, 1977, 15, 848.
Srivastava et al., J. Org. Chem., 1977, 43, 1555.

*Primary Examiner*—Mary C. Lee
*Assistant Examiner*—Joseph K. McKane
*Attorney, Agent, or Firm*—Peggy A. Climenson

[57] ABSTRACT

5-Heterocyclic 2-(2-imidazolin-2-yl)pyridine compounds which are effective for the control of undesirable plant species are described. Also described are a method for the herbicidal use of said compounds and a method for their preparation.

2 Claims, No Drawings

5-HETEROCYCLIC 2-(2-IMIDAZOLIN-2-YL)PYRIDINES, USEFUL AS HERBICIDAL AGENTS AND METHODS FOR THE PREPARATION THEREOF

This is a divisional of co-pending application Ser. No. 07/457,606 filed Dec. 27, 1989 now U.S. Pat. No. 5,039,333.

BACKGROUND OF THE INVENTION

Arylimidazolinones are a class of potent herbicides useful in the control of undesirable plant species in agronomic crops. 2-(2-Imidazolin-2-yl)-pyridines and quinolines and their use are disclosed in U.S. Pat. No. 4,798,619. U.S. patent application Ser. No. 139,996 filed Dec. 31, 1987 discloses 5(and/or 6)substituted 2 TM (2-imidazolin-2-yl)nicotinic acids, esters and salts. Imidazolinyl benzoic acids, esters and salts and their use are disclosed in U.S. Pat. No. 4,188,487.

A process for the preparation of 2-(2-imidazolin-2-yl)-3-pyridine and -3-quinolinecarboxylic acids are disclosed in U.S. Pat. No. 4,758,667.

It is an object of the present invention to provide 5-heterocyclic 2-(2-imidazolin-2-yl)pyridine compounds that are highly effective for controlling undesirable plant species.

SUMMARY OF THE INVENTION

The present invention describes 5-heterocyclic 2-(2-imidazolin-2-yl)pyridine compounds that are highly effective herbicidal agents useful for the control of undesirable plant species and methods for their preparation.

The 5-heterocyclic 2-(2-imidazolin-2-yl)-pyridine compounds of the present invention have the structural formula illustrated as formula I:

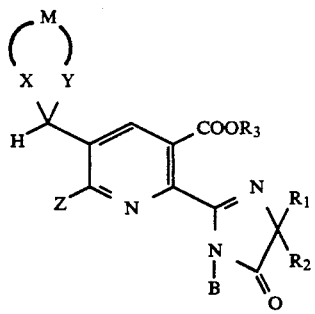

(I)

wherein
$R_1$ is $C_1$–$C_4$ alkyl;
$R_2$ is $C_1$–$C_4$ alkyl or $C_3$–$C_6$ cycloalkyl, and when $R_1$ and $R_2$ are taken together with the carbon to which they are attached they may represent $C_3$–$C_6$ cycloalkyl;
$R_3$ is hydrogen;
  $C_1$–$C_6$ is alkyl optionally substituted with one of the following groups: $C_1$–$C_3$ alkoxy, halogen or phenyl,
  $C_3$–$C_6$ alkyl optionally substituted with one of the following groups: $C_1$–$C_3$ alkoxy, halogen or phenyl,
  $C_3$–$C_6$ alkenyl optionally substituted with one of the following groups: $C_1$–$C_3$ alkoxy, halogen or phenyl,
  $C_3$–$C_6$ alkenyl optionally substituted with one of the following groups: $C_1$–$C_3$ alkoxy, phenyl or halogen,
  $C_3$–$C_6$ alkynyl,
  $C_3$–$C_6$ cycloalkyl optionally substituted with $C_1$–$C_3$ alkyl or
  a cation of alkali metals, ammonium or organic ammonium;
X and Y are each independently oxygen, sulfur or $NR_4$;
$R_4$ is hydrogen, $C_1$–$C_6$ alkyl optionally substituted with $C_1$–$C_4$ alkoxy or 1-3 halogens, $SO_2R_5$, $COR_5$, $CO_2R_5$ or $CONR_5R_5$;
$R_5$ is hydrogen, $C_1$–$C_6$ alkyl optionally substituted with 1-3 halogens, or $C_2$–$C_6$ alkenyl;
M is $C_2$–$C_5$ alkylene optionally substituted with 1 or 2 $C_1$–$C_4$ alkyl groups, $C_1$–$C_4$ alkoxy, halogen, $CO_2R_6$ or oxo, and optionally interrupted by one oxygen or one sulfur,
  $C_2$ alkenylene optionally substituted with 1 or 2 $C_1$–$C_4$ alkyl groups or $CO_2R_6$;
  $C_3$ alkenylene optionally substituted with 1 or 2 $C_1$–$C_4$ alkyl groups, CO or oxo,
  methyleneamino, optionally substituted with $C_1$–$C_4$ alkyl or $CO_2R_6$, or
  a single bond, with the proviso that both X and Y are $NR_4$,
provided that the ring formed by M, X and Y and the carbon to which both X and Y are attached is no more than 8 atoms and provided that when the substituents on M are either alkoxy or halogen the substituted carbon is not bound to X or Y;
$R_6$ is hydrogen, methyl or ethyl;
Z is hydrogen, halogen, $C_1$–$C_6$ alkoxy, or $C_1$–$C_6$ alkyl optionally substituted with $C_1$–$C_4$ alkoxy or halogen;
B is hydrogen or $COR_7$, provided that when B is $COR_7$, $R_3$ is other than hydrogen or a cation;
$R_7$ is $C_1$–$C_5$ alkyl or phenyl optionally substituted with halogen, nitro or methoxy;
the N-oxides thereof, when $R_3$ is not unsaturated alkyl and when M is not alkenylene;
the optical isomers thereof, when $R_1$ and $R_2$ represent different substituents; the acid addition salts thereof, when $R_3$ is other than a cation and the tautomers thereof.

The present invention also relates to a novel substituted imidazopyrrolopyridinediones illustrated by formulas II and III, carbamoyl nicotinic acids, esters and salts depicted by formula IV and pyridinecarboxylic acids, diesters and salts depicted by formula V.

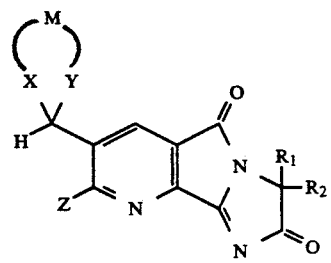

(II)

-continued

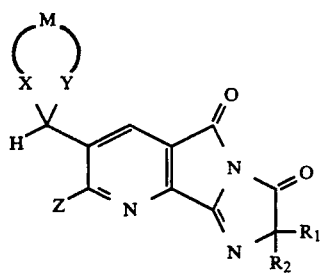
(II)

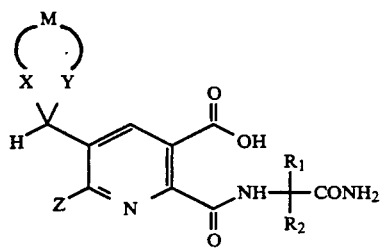
(IV)

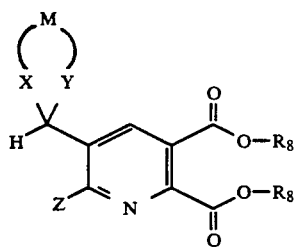
(V)

In the above structures II-V, M X, Y, Z, $R_1$ and $R_2$ are as described above and $R_8$ is $C_1$-$C_4$ alkyl.

Potent herbicides, such as the imidazolinone family of herbicides, are highly desirable for use in agronomic practice because their high potency implies a low use rate combined with effective weed control. A low use rate means increased safety for the farmer and the environment. However, increased crop injury inherent in high herbicidal potency means the range of agronomic crops in which weeds can be controlled can be limited. Surprisingly, it has been found that the herbicidal imidazolinone compounds of the present invention demonstrate enhanced tolerance for sensitive crop species while retaining effective weed control.

DETAILED DESCRIPTION OF THE INVENTION

The 5-heterocyclic 2-(2-imidazolin-2-yl)pyridine compounds of the present invention are effective in the control of undesirable plant species.

The 5-heterocyclic 2-(2-imidazolin-2-yl)pyridine compounds of the present invention are represented by formula I:

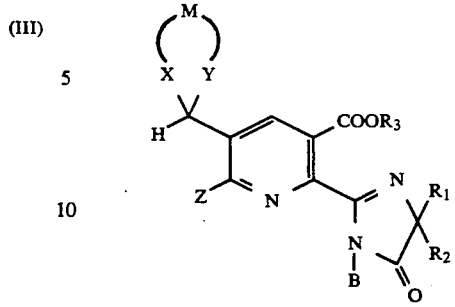
(I)

wherein
$R_1$ is $C_1$-$C_4$ alkyl;
$R_2$ is $C_1$-$C_4$ alkyl or $C_3$-$C_6$ cycloalkyl and when $R_1$ and $R_2$ are taken together with the carbon to which they are attached they may represent $C_3$-$C_6$ cycloalkyl;
$R_3$ is hydrogen,
  $C_1$-$C_6$ alkyl optionally substituted with one of the following groups: $C_1$-$C_3$ alkoxy, halogen or phenyl,
  $C_3$-$C_6$ alkenyl optionally substituted with one of the following groups: $C_1$-$C_3$ alkoxy, phenyl or halogen,
  $C_3$-$C_6$ alkynyl,
  $C_3$-$C_6$ cycloalkyl optionally substituted with $C_1$-$C_3$ alkyl or
  a cation of alkali metals, ammonium or organic ammonium;
X and Y are each independently oxygen, sulfur or $NR_4$;
$R_4$ is hydrogen, $C_1$-$C_6$ alkyl optionally substituted with $C_1$-$C_4$ alkoxy or 1-3 halogens, SO $COR_5$, $CO_2R_5$ or $CONR_5R_5$;
$R_5$ is hydrogen, $C_1$-$C_6$ alkyl optionally substituted with 1-3 halogens, or $C_2$-$C_6$ alkenyl;
M is $C_2$-$C_5$ alkylene optionally substituted with 1 or 2 $C_1$-$C_4$ alkyl groups, $C_1$-$C_4$ alkoxy, halogen, $CO_2R_6$ or oxo, and optionally interrupted by one oxygen or one sulfur,
  $C_2$ alkenylene optionally substituted with 1 or 2 $C_1$-$C_4$ alkyl groups or $CO_2R_6$,
  $C_3$ alkenylene optionally substituted with 1 or 2 $C_1$-$C_4$ alkyl groups, $CO_2R_6$ or oxo,
  methyleneamino, optionally substituted with $C_1$-$C_4$ alkyl or $CO_2R_6$, or
  a single bond, with the proviso that both X and Y are $NR_4$,
provided that the ring formed by M, X and Y and the carbon to which both X and Y are attached is no more than 8 atoms and provided that when the substituents on M are either alkoxy or halogen the substituted carbon is not bound to X or Y;
$R_6$ is hydrogen, methyl or ethyl;
Z is hydrogen, halogen, $C_1$-$C_6$ alkoxy, or $C_1$-$C_6$ alkyl optionally substituted with $C_1$-$C_4$ alkoxy or halogen;
B is hydrogen or $COR_7$, provided that when B is $COR_7$, $R_3$ is other than hydrogen or a cation;
$R_7$ is $C_1$-$C_5$ alkyl or phenyl optionally substituted with halogen, nitro or methoxy;
the N-oxides thereof, when $R_3$ is not unsaturated alkyl and when M is not alkenylene;
the optical isomers thereof, when $R_1$ and $R_2$ represent different substitutents;
the acid addition salts thereof, when $R_3$ is other than a cation and the tautomers thereof.

A preferred group of 5-heterocyclic 2-(2-imidazolin-2-yl)pyridine compounds that exhibit excellent herbicidal activity one having structural formula I as described above and
wherein
$R_1$ is methyl;
$R_2$ is isopropyl;
$R_3$ is hydrogen, $C_1-C_6$ alkyl or a cation of alkali metals, ammonium or organic ammonium;
B is hydrogen and
Z is hydrogen, $C_1-C_4$ alkyl, $C_1-C_4$ alkoxy or halogen.

Another preferred group of 5-heterocyclic 2-(2-imidazolin-2-yl)pyridine compounds of formula I is one wherein
$R_1$ is methyl;
$R_2$ is isopropyl;
$R_3$ is hydrogen, $C_1-C_6$ alkyl or a cation of alkali metals, ammonium or organic ammonium;
B is hydrogen;
Z is hydrogen;
M is unsubstituted alkylene and
X and Y are oxygen.

The seasonal rotation of crops from one field to another is a common agricultural practice. Replacement crops often vary in their tolerance to the herbicides used to control weeds in the previous crops planted in any given field. This variance in tolerance limits the crops to be rotated and/or the types of herbicides used. However the 5-heterocyclic 2-(2-imidazolin-2-yl)pyridine compounds of the present invention when used in rotational agronomic conditions, demonstrate an improved tolerance for sensitive replacement crop species while retaining highly effective weed control in the presence of the imminent crop species.

Certain 5-heterocyclic pyridine compounds of formula V can be prepared by esterfication and halogenation of 5-methyl-2,3-pyridinedicarboxylic acid to yield both a 5-(dihalomethyl)-2,3-pyridinedicarboxylate first intermediate, having the structural formula VIII, and a 5-(halomethyl)-2,3-pyridinedicarboxylate second intermediate of formula IX. Reacting the formula VIII, first intermediate with a loweralkyl alcohol and silver nitrate yields a 5-formyl-2,3-pyridinedicarboxylate, 5-diloweralkyl acetal having the structural formula X. Alternatively, reacting the formula VIII first intermediate with water and silver nitrate yields a 5-formyl-2,3-pyridinedicarboxylate of formula XI. Reacting a formula IX 5-halomethyl-2,3-pyridinedicarboxylate with dimethyl sulfoxide and silver tetrafluoroborate also yields the desired formula XI compound. Said formula XI compound can be converted to the formula X diloweralkyl acetal by reaction with a loweralkyl alcohol, loweralkylorthoformate and an acid. Both the formula XI compounds and the formula X diloweralkyl acetals are converted to 5-heterocyclic pyridine compounds of formula V by reaction with the appropriate reagent having the structural formula VII $$HX-M-YH \tag{VII}$$

wherein M, X and Y are as described for formula I. Reacting a 5-(dihalomethyl)-2,3-pyridinedicarboxylate with silver nitrate and the appropriate formula VII reagent yields a 5-heterocyclic-2,3-pyridinedicarboxylate of formula V. The above-described reaction schemes are illustrated in Flow Diagram I.

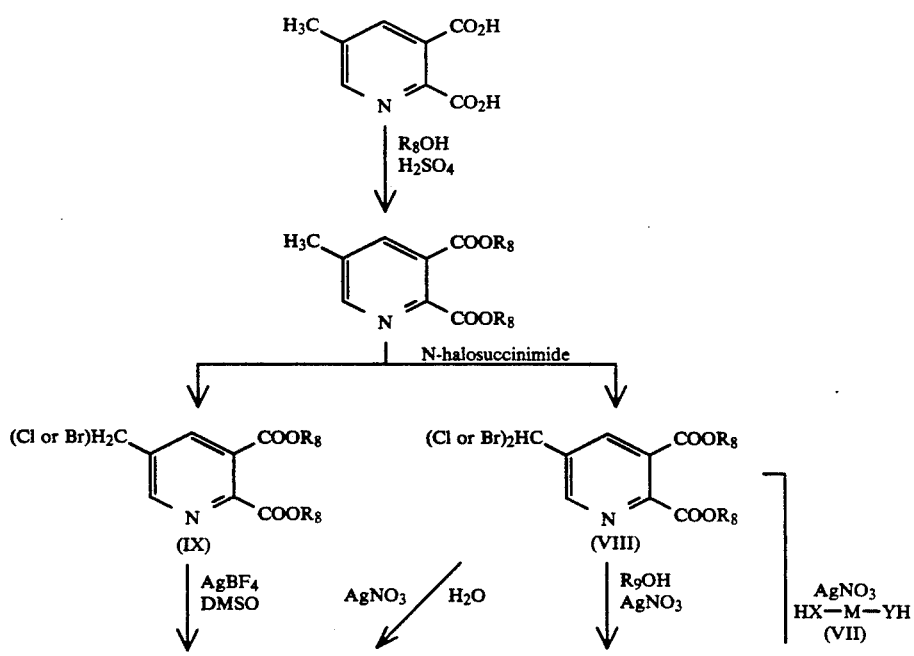

Flow Diagram I

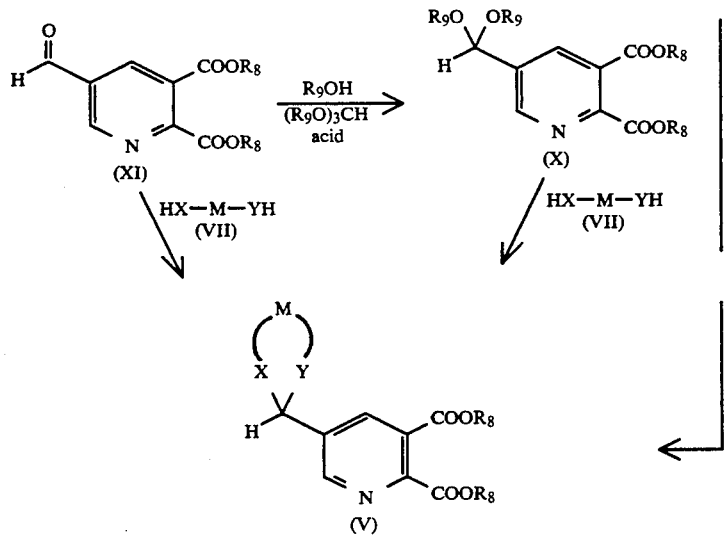

In flow diagram I, X, Y, and M are as described for formula I and $R_8$ and $R_9$ are $C_1$–$C_4$ alkyl.

Formula V compounds and methods of preparation thereof are described in co-pending U.S. patent application Ser. No. 07/457,606 filed concurrently herewith and incorporated herein by reference thereto.

Formula I compounds of the present invention may be prepared by the reaction of a formula V 5-heterocyclic-2,3-pyridinedicarboxylate with an aminocarboxamide and a strong base, such as an alkali metal butoxide followed by acidification to pH 2.0–4.0, to give the desired formula I compound as illustrated below in Flow Diagram II.

Flow Diagram II

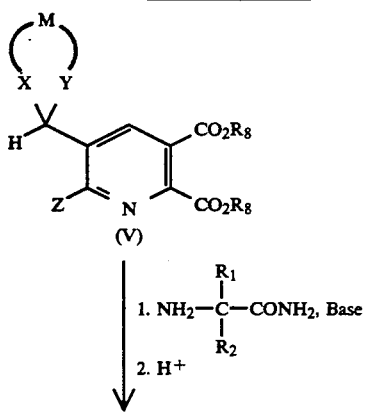

-continued
Flow Diagram II

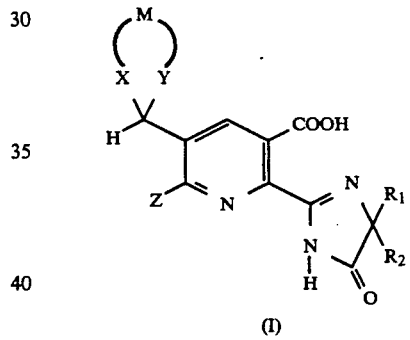

Alternatively, formula I 5-heterocyclic 2-(2-imidazolin-2-yl)pryidine compounds may be prepared by saponification of a formula V pyridinedicarboxylate to give the corresponding dicarboxylic acid (formula XVII), reaction of said formula XVII dicarboxylic acid with acetic anhydride to give the corresponding anhydride of formula XVIII, reaction of the formula XVIII anhydride with at least an one equivalent of an aminocarboxamide to yield a compound having the structural formula XIX and reaction of the formula XIX compound with a base followed by acidification to pH 2.0–4.0 to yield the desired formula I compound as illustrated below in Flow Diagram III.

Flow Diagram III

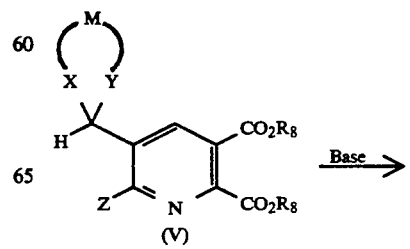

-continued
Flow Diagram III

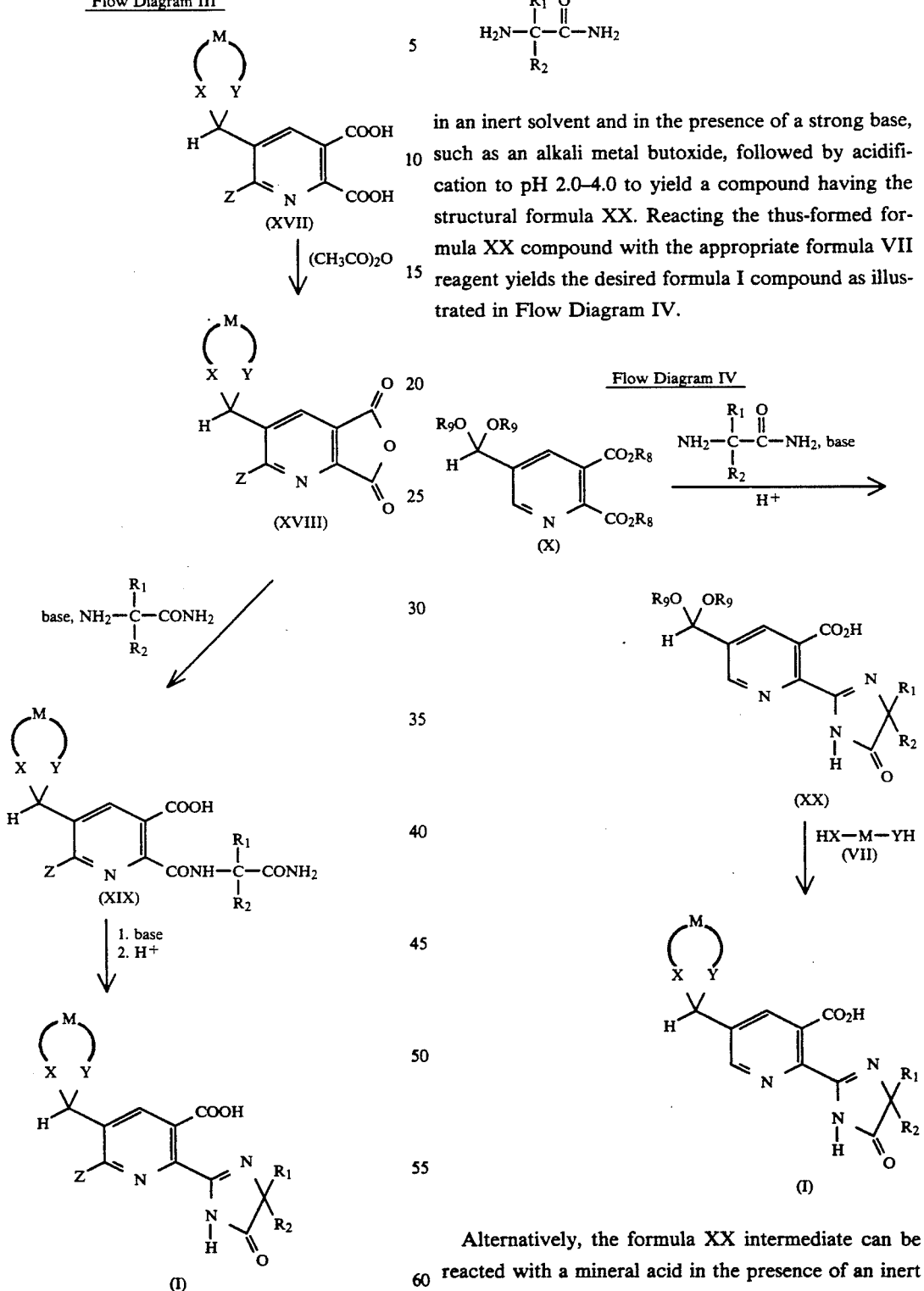

in an inert solvent and in the presence of a strong base, such as an alkali metal butoxide, followed by acidification to pH 2.0–4.0 to yield a compound having the structural formula XX. Reacting the thus-formed formula XX compound with the appropriate formula VII reagent yields the desired formula I compound as illustrated in Flow Diagram IV.

Certain 5-hetrocyclic 2-(2-imidazolin-2-yl)-pyridine compounds of formula I can be prepared by reacting a formula X 5-formyl-2,3-pyridinedicarboxylate, 5-diloweralkylacetal with an aminocarboxamide having the structure.

Alternatively, the formula XX intermediate can be reacted with a mineral acid in the presence of an inert organic solvent to give the corresponding 5-formyl-2-(imidazolin-2-yl)nicotinic acid having the structural formula XXI. Reacting the formula XXI compound with the appropriate formula VII reagent yields the desired formula I compound as illustrated below in Flow Diagram V

Flow Diagram V

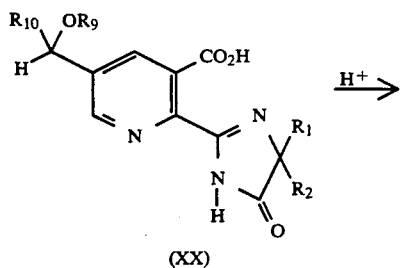

(XX)

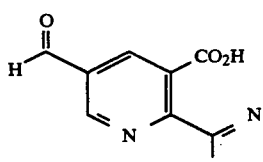 H+

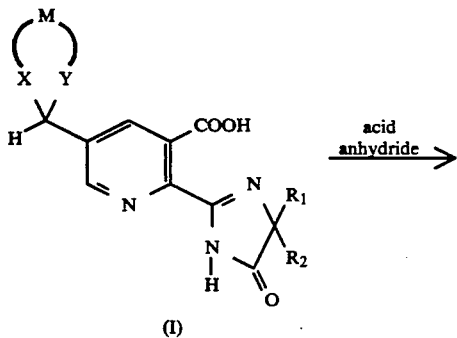

(XXI)

HX—M—YH (VII)

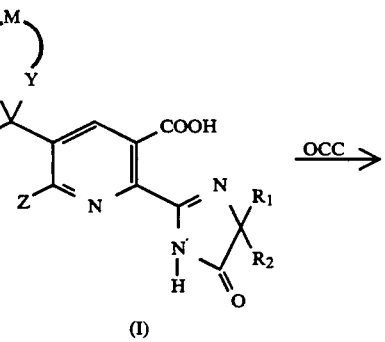

(I)

Formula II 5H-imidazo[1',2':1,2]pyrrolo[3,4-b]pyridine-2(3H), 5-dione compounds of the present invention may be prepared by the reaction of a formula I 5-heterocyclic 2-(2-imidazolin-2-yl)pyridine compound, wherein $R_3$ is hydrogen, with an acid anhydride as shown below:

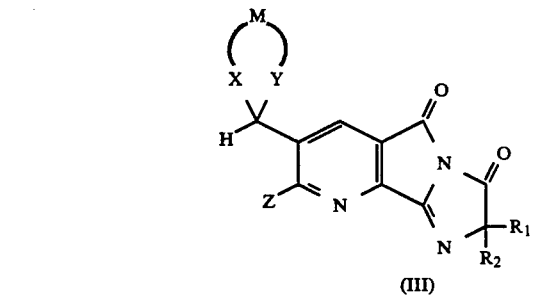

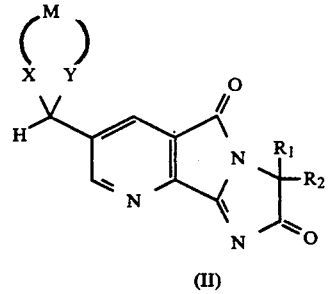

(II)

Formula III 5H-imidazo[1',2':1,2]pyrrolo[3,4-b]pyridine-3(2H), 5-dione compounds of the present invention can be prepared by the reaction of formula I 5-heterocyclic 2-(2-imidazolin-2-yl)pyridine compounds, wherein $R_3$ is hydrogen, with dicyclohexylcarbodiimide in the presence of a solvent as shown below.

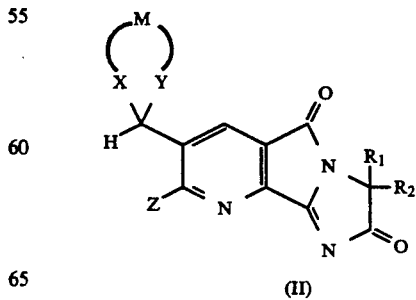

(I)

OCC →

(III)

Certain formula I 5-heterocyclic 2-(2-imidazolin-2-yl)pyridine compounds wherein $R_3$ is not hydrogen can be prepared by reacting the formula II or formula III dione with the appropriate alkoxide as shown below.

(II)

or

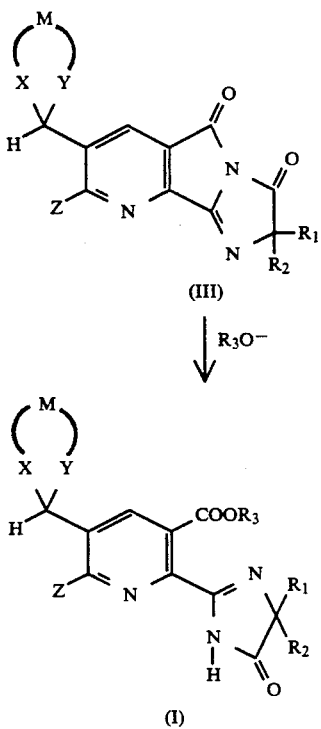

The formula I 5-heterocyclic 2-(2-imidazolin-2-yl)pyridine compounds of the present invention are effective herbicidal agents useful for the control of a wide variety of monocotyledonous and dicotyledonous plants. These compounds are effective for controlling weeds native to both dry land and wet land areas. The compounds are effective in controlling the above-said plants when applied to the foliage thereof or to soil or water containing seeds or other propagating organs of said plants such as stolons, tubers or rhizomes, at rates of from about 0.016 to 2.0 kg/ha.

Since the formula I 5-heterocyclic 2-(2-imidazolin-2-yl)pyridine compounds, wherein $R_3$ is a salt-forming cation, are water soluble, these compounds can simply be dispersed in water and applied as a dilute aqueous spray to the foliage of plants or to soil containing propagating organs thereof. These salts also lend themselves to formulation as flowable concentrates.

The formula I 5-heterocyclic 2-(2-imidazolin-2-yl)pyridines can also be formulated as emulsifiable concentrates, wettable powders, granular formulations, flow concentrates and the like.

A typical emulsifiable concentrate can be prepared by dissolving about 5% to 25% by weight of the active ingredient in about 65% to 90% by weight of N-methylpyrrolidone, isophorone, butyl cellosolve, methylacetate or the like and dispersing therein about 5% to 10% by weight of a nonionic surfactant such as an alkylphenoxy polyethoxy alcohol. This concentrate is dispersed in water for application as a liquid spray.

Wettable powders can be prepared by grinding together about 20% to 45% by weight of a finely divided carrier such as kaolin, bentonite, diatomaceous earth, attapulgite, or the like, 45% to 80% by weight of the active compound, 2% to 5% by weight of a dispersing agent such as sodium lignosulfonate and 2% to 5% by weight of a nonionic surfactant, such as octylphenoxy polyethoxy ethanol, nonylphenoxy polyethoxy ethanol or the like.

Where soil treatments are involved, the compounds may be prepared and applied as granular products. Preparation of the granular product can be achieved by dissolving the active compound in a solvent such as methylene chloride, N-methylpyrrolidone or the like and spraying the thus prepared solution on a granular carrier such as corncob grits, sand, attapulgite, kaolin or the like.

The granular product thus prepared generally comprises about 3% to 20% by weight of the active ingredient and about 97% to 80% by weight of the granular carrier.

A typical flowable liquid can be prepared by admixing about 40% by weight of the active ingredient with about 2% by weight of a gelling agent such as bentonite, 3% by weight of a dispersing agent such as sodium lignosulfonate, 1% by weight of polyethylene glycol and 54% by weight of water.

In order to facilitate a further understanding of the invention, the following examples are presented primarily for the purpose of illustrating more specific details thereof. The invention is not to be deemed limited thereby except as defined in the claims. IR and NMR designate infrared and proton nuclear magnetic resonance, respectively.

EXAMPLE 1

Preparation of Dimethyl 5-(dibromomethyl)-2,3-ovridinedicarboxylate And Dimethyl 5-(bromomethyl) 2,3-pyridinedicarboxylate

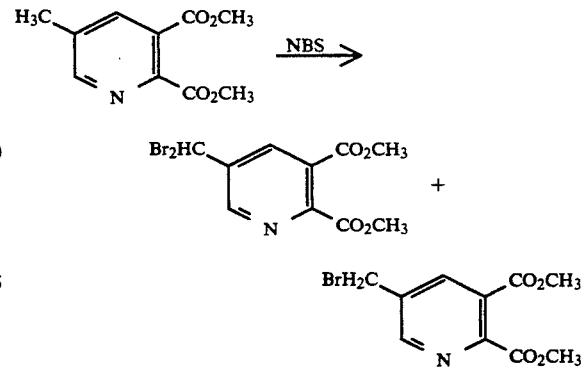

N-bromosuccinimide (83.06 g, 0.46 mol) and benzoyl peroxide (11.28 g, 0.046 mol) are added, in 5 portions over a 7 hour period, to a solution of 5-methyl-2,3-pyridinedicarboxylic acid, dimethyl ester (42.5 g, 0.20 mol) in carbon tetrachloride heated at reflux temperature. The reaction mixture is heated at reflux temperature for 2 hours, cooled to room temperature, filtered and the solids are washed with methylene chloride. The filtrate is washed sequentially with 5% sodium metabisulfite solution and 5% sodium bicarbonate solution, dried over anhydrous magnesium sulfate and concentrated in vacuo to give an oil. The oil is chromatographed on silica gel using 16% ethyl acetate in hexanes and 33% ethyl acetate in hexanes as eluant to give dimethyl 5-(dibromomethyl)-2-3-pyridinedicarboxylate as a white solid, (47.2 g, 64%), mp 61°-65° C. identified by IR and NMR spectral analyses and dimethyl 5-(bromomethyl)2,3-pyridinedicarboxylate (11.4, 20%) as a clear oil, identified by IR and NMR spectral analyses.

EXAMPLE 2

Preparation of Dimethyl 5-formylpyridine-2,3-dicarboxylate

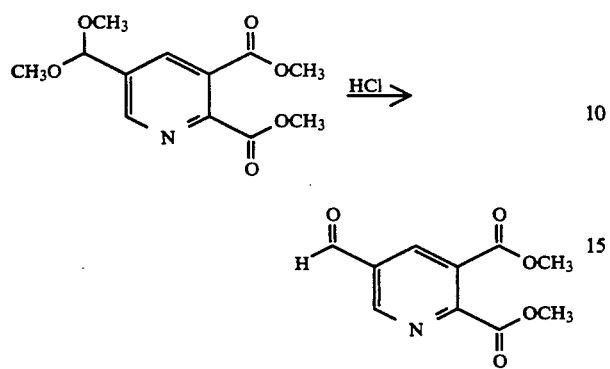

A solution of dimethyl 5-dimethoxymethylpyridine-2,3-dicarboxylate (6.57 g, 0.024 mol) in 2N HCl (15 mL) and tetrahydrofuran (25 mL) is stirred at reflux temperature for 2 hours. The tetrahydrofuran is removed in vacuo, the aqueous solution is diluted with water (to 30 mL) and extracted with methylene chloride. The combined methylene chloride extracts are dried over anhydrous magnesium sulfate and concentrated in vacuo to yield the title compound (4.51 g, 82%) as a yellow solid, mp 75°–77° C., identified by IR and NMR spectral analyses.

Using the above procedure and employing dimethyl 5-dimethoxymethyl-6-chloropyridine-2,3-dicarboxylate as starting materials affords dimethyl 5-formyl-6-chloropyridine-2,3-dicarboxylate as an oil.

EXAMPLE 3

Preparation of Dimethyl 5-formyl-6-methoxypyridine-2,3-dicarboxylate

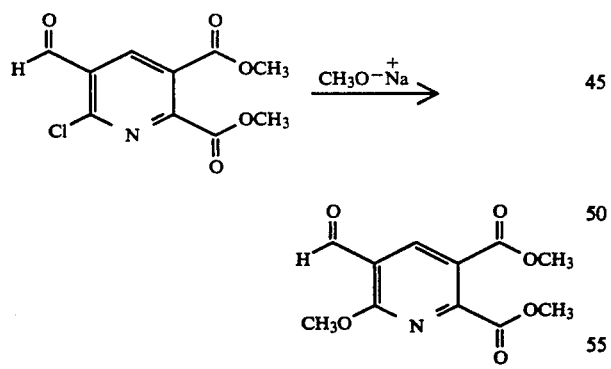

A solution of dimethyl 6-chloro-5-formylpyridine-2,3-dicarboxylate (1.0 g, 0.0039 mol) in methanol (10 mL) is added to sodium methoxide (0.42 g, 0.0078 mol) in methanol (2 mL). The resulting mixture is stirred for 15 hours at 90° C. After cooling to room temperature, the reaction mixture is acidified to pH 3.0 with acetic acid. The reaction is poured into methylene chloride, washed with water, dried over anhydrous magnesium sulfate and concentrated in vacuo to yield the title compound (0.62 g, 63%) as an orange oil, identified by IR and NMR spectral analyses.

EXAMPLE 4

Preparation of Dimethyl 5 formyl-2,3-pyridinedicarboxylate, 5-dimethyl acetal

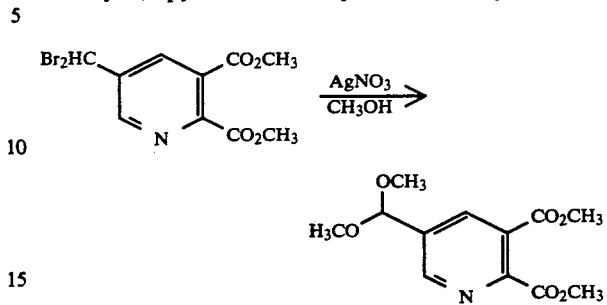

Silver nitrate (134.49 g, 0.816 mol) is added to a solution of 5-(dibromomethyl)-2,3-pyridinedicarboxylic acid, dimethyl ester (146.01 g, 0.398 mol) and methanol. The reaction mixture is stirred for 30 minutes at 25° C. then for 1 hour and 30 minutes at reflux temperature. The reaction mixture is cooled to room temperature, filtered through a pad of diatomaceous earth and the diatomaceous earth is rinsed with methanol. The filtrate is concentrated in vacuo to give an oil. The oil is dissolved in methylene chloride, washed with 5% sodium bicarbonate solution, dried over anhydrous magnesium sulfate and concentrated in vacuo to give an oil. The residue oil is chromatographed using silica gel, 16% ethyl acetate in hexanes and 50% ethyl acetate in hexanes as eluant to yield the title compound as a clear oil, (98.39 g, 92%), identified by IR and NMR spectral analyses.

EXAMPLE 5

Preparation of Dimethyl 5-dimethoxymethylpyridine-2,3-dicarboxylate

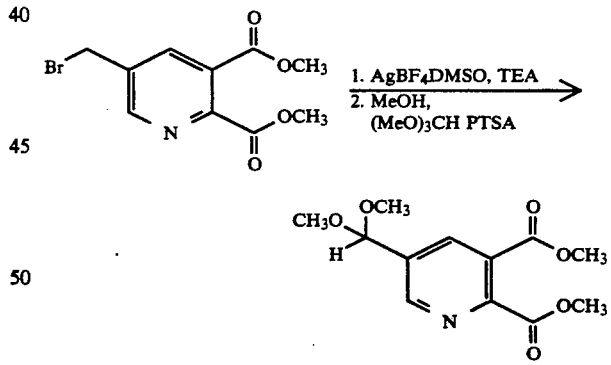

To a solution of dimethyl 5-bromomethylpyridine-2,3-dicarboxylate (10.55 g, 0.0366 mol) in dimethylsulfoxide (50 mL) is added solid silver tetrafluoroborate (8.91 g, 0.0458 mol). The resulting mixture is stirred for 1.5 hours at 80° C.–90° C., then triethylamine (6.75 mL 0.458 mol) is added and the reaction mixture is stirred for an additional 1 hour at 80° C. The reaction is filtered through a pad of diatomaceous earth and the diatomaceous earth is rinsed with methanol. The filtrate is concentrated in vacuo and the crude product is dissolved in methanol (100 mL) and trimethylorthoformate (15 mL). A catalytic amount of para-toluenesulfonic acid is added and the reaction mixture is stirred at reflux temperature for 4.5 days. The reaction mixture is concentrated in vacuo and diluted with H₂O and passed through a pad of C-18 silica gel. Elution with methanol in water affords a crude product, which is purified by chromatography on silica gel using ethyl acetate in hexanes as eluant to yield the title compound (1.96 g, 20%) as a clear oil, identified by IR and NMR spectral analyses.

EXAMPLE 6

Preparation of Dimethyl 5 formylpyridine-2,3 dicarboxylate

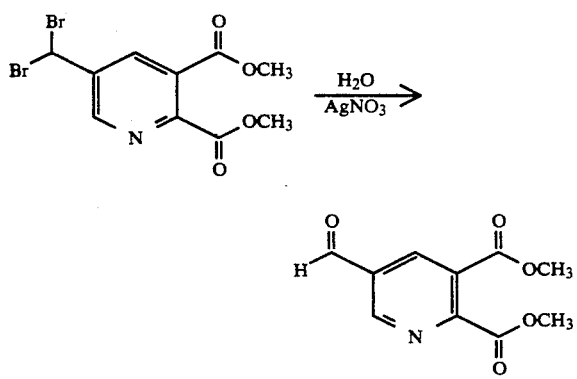

To a solution of dimethyl 5-dibromomethylpyridine-2,3-dicarboxylate (8.32 g, 0.0227 mol) in dioxane (60 mL) and water (20 mL) is added silver nitrate (7.85 g, 0.0476 mol). The resulting slurry is heated at reflux for 3 hours. The reaction mixture is cooled to room temperature, filtered through a pad of diatomaceous earth and the diatomaceous earth is rinsed with tetrahydrofuran. The filtrate is concentrated in vacuo to remove the dioxane and tetrahydrofuran. The resultant aqueous solution is made basic by the addition to saturated aqueous sodium bicarbonate (100 mL) and extracted with methylene dichloride. The combined extracts are dried over anhydrous magnesium sulfate and concentrated in vacuo to give a residue. Chromatography of said residue using silica gel and 33% ethyl acetate in hexanes as eluant yields the title compound as a white solid, (4.31 g, 85%) mp 75° C.-77° C., identified by IR and NMR spectral analyses.

EXAMPLE 7

Preparation of Methyl 2-(1-benzoyl-4-isopropyl-4-methyl-5-oxo-2-imidazolin-2-yl)-5-methylnicotinate

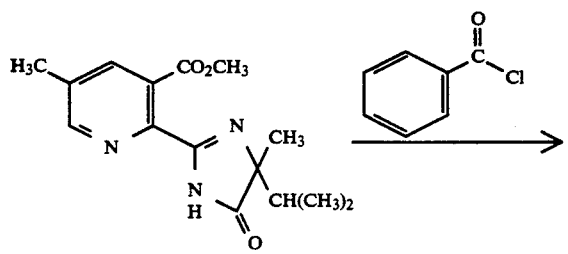

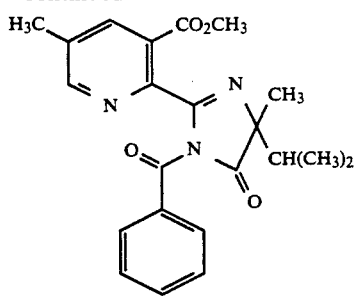

Benzoyl chloride (42.1 mL, 0.363 mol) is added dropwise to a 0° C. solution of 2-(4-isopropyl-4-methyl-5-oxo-2-imidazolin-2-yl)-5-methylnicotinic acid, methyl ester (50 g, 0.173 mol) and 4-dimethylaminopyridine (4.2 g, 0.0344 mol) in pyridine. The reaction mixture is stirred for 1 hour at 0° C. and 4 hours at room temperature. Concentration in vacuo gives a liquid that is dissolved into methylene chloride and washed sequentially with 2 normal hydrochloric acid and saturated sodium bicarbonate solution, dried over anhydrous magnesium sulfate and concentrated in vacuo to yield a solid that upon trituration with ether gives the title compound as a white solid (46.2 g, 68%), mp 104°-106° C., identified by IR and NMR spectral analyses.

EXAMPLE 8

Preparation of Methyl 2-(1-enzoyl-4-isopropyl-4-methyl-5-oxo-2-imidazolin-2-yl)-5-(bromomethyl)-nicotinate

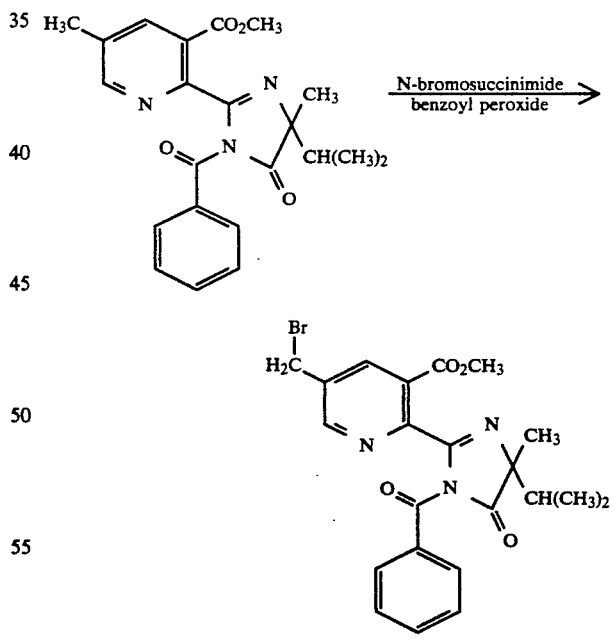

Solid N-bromosuccinimide (22.98 g, 0.129 mol) and benzoyl peroxide (3.12 g, 0.0129 mol) are added to a 25° C. solution of 2-(1-benzoyl-4-isopropyl-4-methyl-5-oxo-2-imidazolin-2-yl)-5-methylnicotinic acid, methyl ester (46.2 g, 0.117 mol) in carbon tetrachloride. The reaction mixture is heated at 70° C. for 16 hours, cooled to room temperature, diluted with methylene chloride, washed sequentially with 5% sodium metabisulfite solution and water, dried over anhydrous magnesium sulfate and concentrated in vacuo to give an oil. The oil is chromatographed using silica gel and hexanes/ethyl acetate (3:1) to (1:1) as eluant to give the title compound as a yellow solid (19.64 g, 35%), mp 88°-119° C., identified by IR and NMR spectral analyses.

EXAMPLE 9

Preparation of Methyl 2-(4-isopropyl-4-methyl-5-oxo-2-imidazolin-2-yl)-5-[(phenylthio)methyl]nicotinate

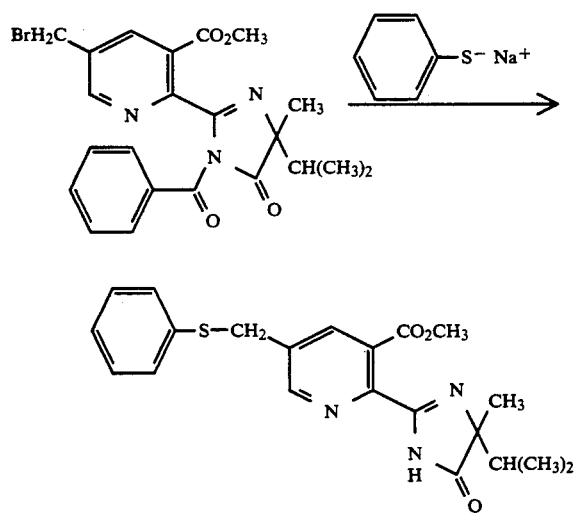

A solution of thiophenol, sodium salt and methanol is added to a solution of 2-(1-benzoyl-4-isopropyl-4-methyl-5-oxo-2-imidazolin-2-yl)-5-(bromomethyl)nicotinic acid, methyl ester (14.08 g, 0.0298 mol) and methanol. The reaction mixture is stirred for 15 hours at room temperature, acidified with ammonium chloride (5 g, 0.0869 mol) and concentrated in vacuo to yield an oil. The oil is chromatographed using silica gel and hexanes/ethyl acetate (3:1) to (1:1) as eluant to give the title compound as a yellow solid (8.32 g, 55%), mp 135°-138° C., identified by IR and NMR spectral analyses.

EXAMPLE 10

Preparation of Methyl 2-(4-isopropyl-4-methyl-5-oxo-2-imidazolin-2-yl)-5-[(phenylsulfinyl)methyl]nicotinate

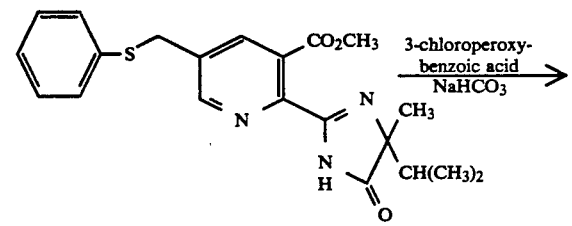

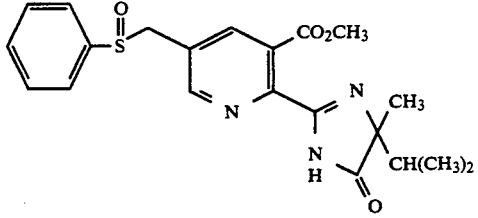

3-Chloroperoxybenzoic acid (20 mL, 0.00252 mol) is added dropwise to a −78° C. solution of 2-(4-isopropyl-4-methyl-5-oxo-2-imidazolin-2-yl)-5-[(phenylthio)methyl]nicotinic acid, methyl ester (1.0 g, 0.00252 mol) and sodium bicarbonate (0.2 g, 0.00238 mol) in methylene chloride. The reaction mixture is stirred at −78° C. for 30 minutes and then at room temperature for 24 hours. The reaction mixture is diluted with 5% sodium metabisulfite solution. The methylene chloride layer is separated, washed with saturated sodium bicarbonate solution, dried over anhydrous magnesium sulfate and concentrated in vacuo to yield a yellow oil. The oil is chromatographed using silica gel and hexanes/ethyl acetate (1:1) to (1:2) to (1:9) and finally 100% ethyl acetate as eluant to give the title compound as a yellow solid (0.97 g, 90%), mp 132°-136° C., identified by IR and NMR spectral analyses.

EXAMPLE 11

Preparation of Methyl 2-(1-acetyl-4-isopropyl-4-methyl-5-oxo-2-imidazolin-2-yl)-5-[hydroxy(phenylthio)methyl]-nicotinate, 5-acetate

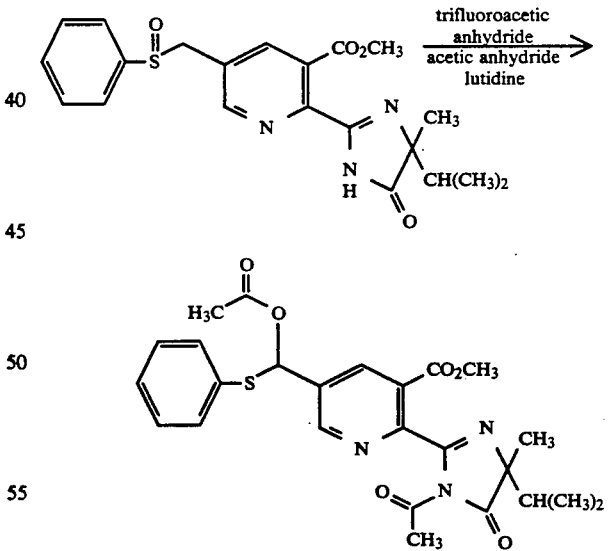

A solution of trifluoroacetaic anhydride (0.85 mL, 0.006 mol) in acetic anhydride is stirred at room temperature for 3 hours. 2-(4-Isopropyl-4-methyl-5-oxo-2-imidazolin-2-yl)-5-[(phenylsulfinyl)methyl]-nicotinic acid, methyl ester (1.0 g, 0.0024 mol) is dissolved into the solution and stirred at room temperature for 15 minutes. Lutidine (840 μL, 0.072 mol) is added and the reaction mixture is stirred at room temperature for 15 minutes. Lutidine (840 μL, 0.072 mol) is added and the reaction mixture is stirred for 2 hours at room temperature. Concentration in vacuo yields an oil which is dissolved into methylene chloride and washed sequentially with 2 normal hydrochloric acid and saturated sodium bicarbonate solution, dried over anhydrous magnesium sulfate and concentrated in vacuo to give the title compound as an orange oil (1.49 g, 100%), identified by IR and NMR spectral analyses.

EXAMPLE 12

Preparation of 5-Formyl-2-(4-isopropyl-4-methyl-5-oxo-2-imidazolin-2-yl)nicotinic acid, 5-(dimethyl acetal)

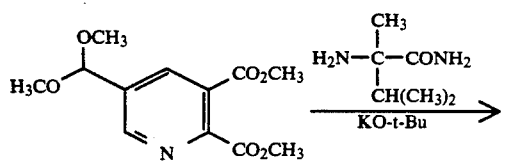

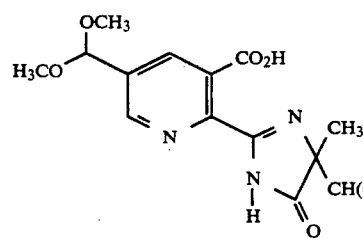

Potassium tert-butoxide (26.55 g, 0.236 mol) is added portionwise to a stirred solution of 5-formyl-2,3-pyridinedicarboxylic acid, dimethyl ester, 5-dimethyl acetal (30.31 g, 0.112 mol) and 2-amino-2,3-dimethyl-butyramide (14.67 g, 0.113 mol) in toluene, the reaction mixture exotherms to about 40° C. The reaction mixture is heated to 80° C, for 1 hour, cooled to room temperature and diluted with water. The layers are separated and the aqueous solution is acidified to pH 3.0 with concentrated hydrochloric acid. The aqueous solution is then extracted with methylene chloride and the combined methylene chloride extracts are dried over anhydrous magnesium sulfate and concentrated in vacuo to give the title compound as a tan solid, (32.12 g, 85%), mp 135°–139° C., identified by IR and NMR spectral analyses.

EXAMPLE 13

Preparation of 5-Formyl-2-(4-isopropyl-4-methyl-5-oxo-2-imidazolin-2-yl)nicotinic acid

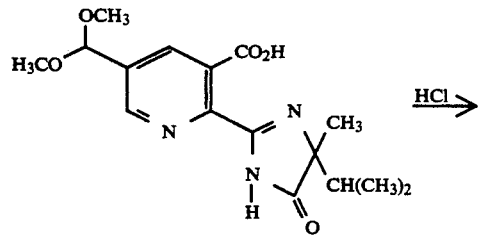

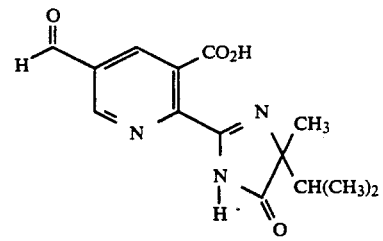

A solution of 5-formyl-2-(4-isopropyl-4-methyl-5-oxo-2-imidazolin-2-yl)nicotinic acid, 5-(dimethyl acetal) (3.65 g, 0.0109 mol) and 2N hydrochloric acid is stirred for 2 hours at room temperature. The pH of the reaction mixture is adjusted to 3.0 with sodium bicarbonate and the water is evaporated in vacuo to give a solid. The solid is triturated with acetone/ethanol (2:1) and removed by filtration. The filtrate is concentrated in vacuo to yield the title compound as a tan solid (3.5 g, 100%), mp 187°–198° C., identified by IR and NMR spectral analyses.

EXAMPLE 14

Preparation of Dimethyl 6-chloro-5-(1,3-dioxolane-2-yl)-2,3-pyridinedicarboxylate

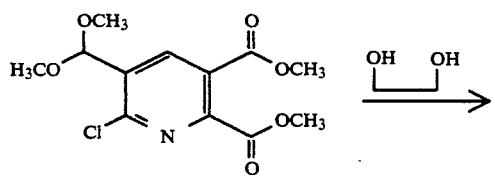

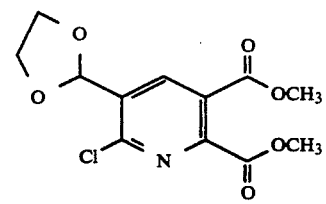

Ethylene glycol (14.3 mL, 0.255 mol), and a catalytic amount of p-toluenesulfonic acid monohydrate is added to a solution of 6-chloro-5-formyl-2,3-pyridinedicarboxylic acid, dimethyl ester, 5-(dimethyl acetal) (15.46 g, 0.051 mol) and toluene. The reaction mixture is heated at reflux temperature for 3 hours, cooled to room temperature, treated with ether, washed with saturated sodium bicarbonate solution, dried over anhydrous magnesium sulfate and concentrated in vacuo to give the title compound as an orange oil (14.27 g, 93% identified by IR and NMR spectral analyses.

EXAMPLE 15

Preparation of Dimethyl 5-(1,3-dioxolan-2-yl)-2,3-pyridinedicarboxylate

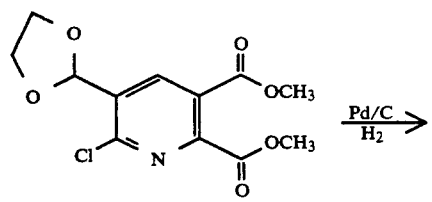

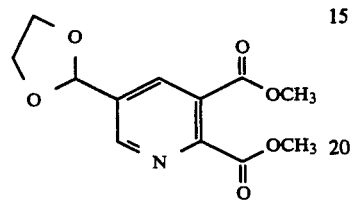

A solution of 6-chloro-5-(1,3-dioxolan-2-yl)-2,3-pyridinecarboxylic acid, dimethyl ester (9.16 g, 0.03 mol) in deoxygenated methanol is added to a Parr flask containing wet palladium on activated carbon and sodium acetate. The flask is placed in a hydrogenator where the reaction mixture absorbs hydrogen. The reaction mixture is then filtered through diatomaceous earth and the flask and diatomaceous earth are rinsed with methanol. The filtrate is concentrated in vacuo and the residual oil is partitioned between methylene chloride and water. The layers are separated and the organic layer is washed with saturated sodium bicarbonate solution, dried over anhydrous magnesium sulfate and concentrated in vacuo to give the title compound as an orange oil (3.53 g, 44%), identified by IR and NMR spectral analyses.

EXAMPLE 16

Preparation of Dimethyl 5-(1,3-Dioxepan-2-yl)-2,2-pyridinedicarboxylate

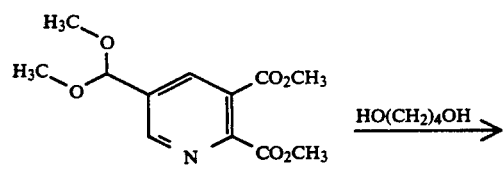

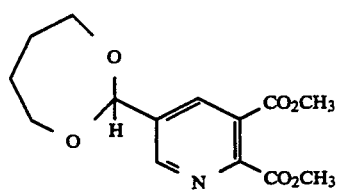

A solution of 5-formyl-2,3-pyridinedicarboxylic acid, dimethyl ester, 5-dimethyl acetal (1.3 g, 0.0048 mol), a catalytic amount of p-toluenesulfonic acid, 1,4-butanediol and toluene is heated at reflux temperature for 2 hours and 30 minutes. The reaction mixture is cooled to room temperature, made basic with sodium bicarbonate and concentrated in vacuo to give a liquid. The liquid is partitioned between methylene chloride and 5% sodium bicarbonate solution. The layers are separated and the aqueous layer is extracted with methylene chloride, the combined methylene chloride extracts are dried over anhydrous magnesium sulfate and concentrated in vacuo to give an oil. The oil is chromatographed using silica gel and hexanes/ethyl acetate (2:1 to 1:1) as eluant to give the title compound as a clear oil (0.88 g, 62%), identified by IR and NMR spectral analyses.

Following the above procedure but using the appropriately substituted 2,3-pyridinecarboxylic acid, dimethyl ester and the appropriate diol or 2-mercaptoethanol, the compounds shown below are obtained.

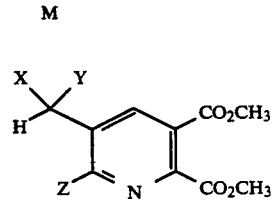

| X | Y | M | Z |
|---|---|---|---|
| O | O | C₄H₈ | H |
| S | O | C₂H₄ | H |
| O | O | C₂H₄ | OCH₃ |
| O | O | C₂H₄ | CH₃ |

EXAMPLE 17

Preparation of Dimethyl 5-(1,2-dimethyl-3-diaziridinyl-2,3-pyridinedicarboxylate

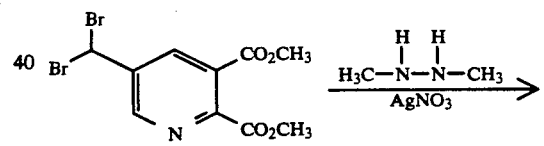

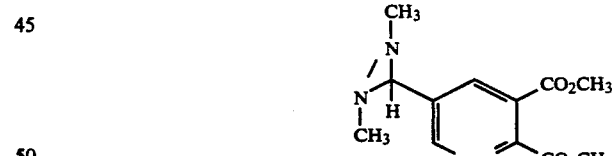

5-(Dibromomethyl)-2,3-pyridinedicarboxylic acid, dimethyl ester (2.0 g, 0.00545 mol), silver nitrate (1.85 g, 0.0109 mol) and 1,2-dimethylhydrazine dihydrochloride salt in pyridine is heated from 25° C. to 100° C. over 50 minutes, then at 100° C. for 1 hour and 45 minutes. Concentration in vacuo gives a liquid that is triturated with water and methylene chloride and filtered. The layers are separated and the aqueous layer is extracted with methylene chloride. The combined methylene chloride extracts are dried over anhydrous magnesium sulfate and concentrated in vacuo to give an oil. The oil is chromatographed using silica gel and hexanes/ethyl acetate (2:1 to 4:3 to 1) as eluant to give the title compound as a yellow oil (0.48 g, 33%), identified by IR and NMR spectral analyses.

EXAMPLE 18

Preparation of Dimethyl 5-(1,3-dithiolan 2-yl)-2,3-pyridinedicarboxylate

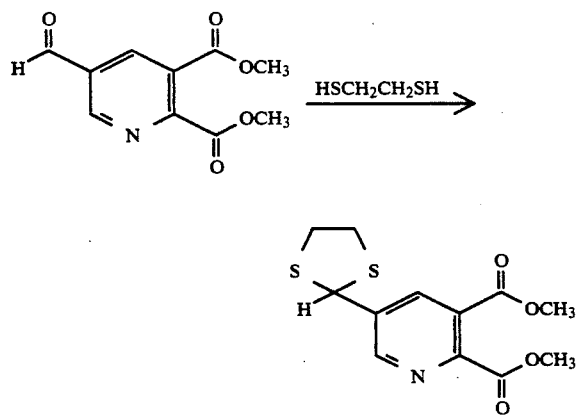

A solution of dimethyl 5-formylpyridine-2,3-dicarboxylate (0.73 g, 0.00327 mol), ethanedithiol (0.357 mL, 0.00425 mol) and a catalytic amount of para-toluenesulfonic acid in chloroform (20 mL) is heated at reflux for 5.5 hours. During this time, water is removed by placement of an addition funnel containing 3 angstrom molecular sieves in between the reaction flask and the reflux condensor. After cooling, the reaction is diluted with methylene chloride (20 mL) and is washed with 10% aqueous sodium carbonate and saturated sodium chloride solutions. The organic solution is dried over anhydrous magnesium sulfate and concentrated in vacuo to give a residue. The residue is purified by chromatography using silica gel and 33% ethyl acetate in hexanes as eluant to yield the title compound as a clear oil (0.66 g, 67%), identified by IR and NMR spectral analyses.

EXAMPLE 19

Preparation of Dimethyl 5-(1-acetyl-3-methyl 2-imidazolidinyl)pyridine-2,3-dicarboxylate

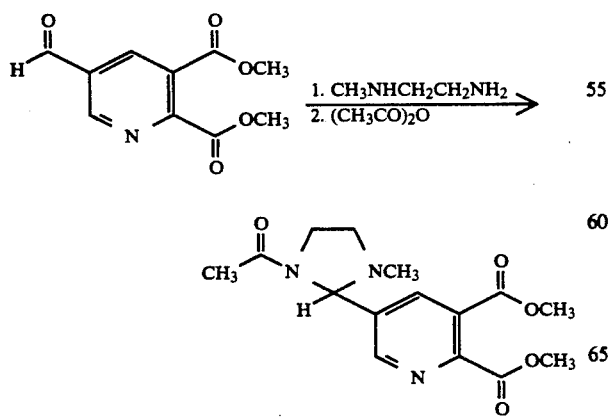

A solution of dimethyl 5-formylpyridine-2,3-dicarboxylate (0.75 g, 0.0036 mol), N-methylethylene diamine (0.38 mL, 0.0044 mol) and a catalytic amount of para-toluenesulfonic acid in toluene (10 mL) is heated at reflux temperature for 3 hours. During this process, water is removed by placement of an addition funnel containing 3 angstrom molecular sieves between the reaction flask and the reflux condensor. The reaction mixture is concentrated in vacuo, dissolved in methylene chloride (30 mL) and is washed with saturated aqueous sodium bicarbonate solution. The organic solution is dried over anhydrous magnesium sulfate and concentrated in vacuo to give a residue. The residue is dissolved in pyridine (10 mL) at 0° C. and treated with acetic anhydride (0.34 mL, 0.0036 mol). The reaction mixture is stirred for 1 hour at 0° C. and for 66 hours at room temperature. The pyridine is removed in vacuo to yield an oil. The oil is dissolved in methylene chloride and washed with saturated aqueous sodium bicarbonate. The organic solution is dried over anhydrous magnesium sulfate, concentrated in vacuo and purified by chromatography using silica gel and 10% triethylamine in ethyl acetate as eluant to yield the title compound (0.66 g, 56%) as a yellow oil, identified by IR and NMR spectral analyses.

Using the above procedure and substituting the appropriate diamine or amino alcohol and the appropriate acylating reagent, the following compounds are obtained.

| X | Y | M |
|---|---|---|
| NCOCH3 | NCH3 | (CH2)2 |
| NCOCH3 | O | (CH2)2 |
| NCO2CH3 | O | (CH2)2 |
| NCO2CH2CH3 | O | (CH2)2 |
| NCON(CH3)2 | O | (CH2)2 |
| NCONHCH(CH3)2 | O | (CH2)2 |
| NCOCH(CH3)2 | O | (CH2)2 |
| NCO2CH2CH3 | O | (CH2)3 |
| NSO2CH3 | O | (CH2)2 |

Using the methods as described above, the following formula V compounds may be prepared.

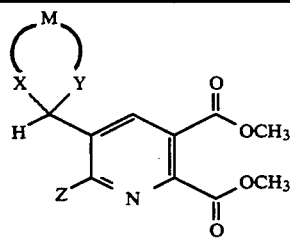

(V)

| X | Y | M | M | mp °C. |
|---|---|---|---|---|
| O | O | (CH₂)₂ | H | oil |
| O | O | CH(CH₃)CH₂ | H | oil |
| O | O | C(CH₃)₂CH₂ | H |  |
| O | O | CH(CH₃)CH(CH₃) | H |  |
| O | O | (CH₂)₃ | H | oil |
| O | O | CH(CH₃)CH₂CH₂ | H |  |
| O | O | CH₂CH(CH₃)CH₂ | H |  |
| O | O | C(CH₃)₂CH₂CH₂ | H |  |
| O | O | CH(CH₃)CH—(CH₃)CH₂ | H |  |
| O | O | CH₂C(CH₃)₂CH₂ | H | oil |
| O | O | (CH₂)₄ | H | oil |
| O | O | CH(CH₃)CH₂CH₂CH₂ | H |  |
| O | O | CH₂CH(CH₃)CH₂CH₂ | H |  |
| O | O | C(CH₃)₂CH₂CH₂CH₂ | H |  |
| O | O | CH(CH₃)CH(CH₃)—CH₂CH₂ | H |  |
| O | O | CH(CH₃)CH₂—CH₂CH(CH₃) | H |  |
| O | O | CH₂C(CH₃)—CH₂CH₂ | H |  |
| O | O | CH₂CH(CH₃)—CH(CH₃)CH₂ | H |  |
| O | O | (CH₂)₅ | H |  |
| O | O | CH₂CH₂OCH₂—CH₂ | H |  |
| O | O | CH₂CH₂SCH₂—CH₂ | H |  |
| O | O | CH₂CH₂SCH₂CH₂ | H |  |
| O | O | CH₂CH(OCH₃)—CH₂ | H |  |
| O | S | (CH₂)₂ | H | oil |
| O | S | CH(CH₃)CH₂ | H |  |
| O | S | C(CH₃)₂CH₂ | H |  |
| O | S | CH(CH₃)CH(CH₃) | H |  |
| O | S | (CH₂)₃ | H |  |
| O | S | CH(CH₃)CH₂CH₂ | H |  |
| O | S | CH₂CH(CH₃)CH₂ | H |  |
| O | S | C(CH₃)₂CH₂CH₂ | H |  |
| O | S | CH(CH₃)CH(CH₃)—CH₂ | H |  |
| O | S | CH(CH₃)CH₂CH(CH₃) | H |  |
| O | S | CH₂C(CH₃)₂CH₂—(CH₃) | H |  |
| O | S | (CH₂)₄ | H |  |
| O | S | CH(CH₃)CH₂—CH₂CH₂ | H |  |
| O | S | CH₂CH(CH₃)—CH₂CH₂ | H |  |
| O | S | C(CH₃)₂CH₂—CH₂CH₂ | H |  |
| O | S | CH(CH₃)CH(CH₃)—CH₂CH₂ | H |  |
| O | S | CH(CH₃)CH₂CH—(CH₃)CH₂ | H |  |
| O | S | CH(CH₃)CH₂CH₂—CH(CH₃) | H |  |
| O | S | CH₂C(CH₃)₂—CH₂CH₂ | H |  |
| O | S | CH₂CH(CH₃)—CH(CH₃)CH₂ | H |  |
| O | S | (CH₂)₅ | H |  |
| O | S | CH₂CH₂OCH₂CH₂ | H |  |
| O | S | CH₂CH₂OCH₂CH₂ | H |  |
| S | S | (CH₂)₂ | H |  |
| S | S | CH(CH₃)CH₂ | H |  |
| S | S | C(CH₃)₂CH₂ | H |  |
| S | S | CH(CH₃)CH(CH₃) | H |  |
| S | S | (CH₂)₃ | H |  |
| S | S | CH(CH₃)CH₂CH₂ | H |  |
| S | S | CH₂CH(CH₃)CH₂ | H |  |
| S | S | C(CH₃)₂CH₂CH₂ | H |  |
| S | S | CH(CH₃)CH(CH₃)—CH₂ | H |  |
| S | S | CH(CH₃)CH₂CH(CH₃) | H |  |
| S | S | CH₂C(CH₃)₂CH₂ | H |  |
| S | S | (CH₂)₄ | H |  |
| S | S | CH(CH₃)CH₂CH₂CH₂ | H |  |
| S | S | CH₂CH(CH₃)CH₂CH₂ | H |  |
| S | S | C(CH₃)₂CH₂CH₂CH₂ | H |  |
| S | S | CH(CH₃)CH(CH₃)—CH₂CH₂ | H |  |
| S | S | CH(CH₃)CH₂CH—(CH₃)CH₂ | H |  |
| S | S | CH(CH₃)CH₂CH₂—CH(CH₃) | H |  |
| S | S | CH₂C(CH₃)₂—CH₂CH₂ | H |  |
| S | S | CH₂CH(CH₃)—CH(CH₃)CH₂ | H |  |
| S | S | (CH₂)₅ | H |  |

-continued

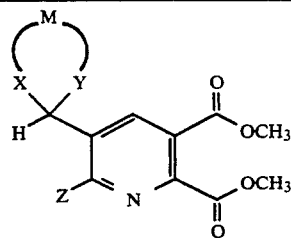

(V)

| X | Y | M | M | mp °C |
|---|---|---|---|---|
| S | S | CH₂CH₂OCH₂CH₂ | H | |
| S | S | CH₂CH₂OCH₂CH₂ | H | |
| O | O | (CH₂)₂ | CH₃ | oil |
| O | O | (CH₂)₂ | CH₂CH₃ | |
| O | O | (CH₂)₂ | CH(CH₃)₂ | |
| O | O | (CH₂)₂ | CH₂CH₂CH₃ | |
| O | O | CH(CH₃)CH₂ | CH₃ | |
| O | O | C(CH₃)₂CH₂ | CH₃ | |
| O | O | (CH₂)₃ | CH₃ | |
| O | O | (CH₂)₄ | CH₃ | |
| O | S | (CH₂)₂ | CH₃ | |
| O | S | (CH₂)₂ | CH₂CH₃ | |
| O | S | (CH₂)₂ | CH(CH₃)₂ | |
| O | S | (CH₂)₂ | CH₂CH₂CH₃ | |
| O | S | CH(CH₃)CH₂ | CH₃ | |
| O | S | C(CH₃)₂CH₂ | CH₃ | |
| O | S | (CH₂)₃ | CH₃ | |
| O | S | (CH₂)₄ | CH₃ | |
| S | S | (CH₂)₂ | CH₃ | |
| S | S | (CH₂)₂ | CH₂CH₃ | |
| S | S | (CH₂)₂ | CH(CH₃)₂ | |
| S | S | (CH₂)₂ | CH₂CH₂CH₃ | |
| S | S | CH(CH₃)CH₂ | CH₃ | |
| S | S | C(CH₃)₂CH₂ | CH₃ | |
| S | S | (CH₂)₃ | CH₃ | |
| S | S | (CH₂)₄ | CH₃ | |
| O | O | (CH₂)₂ | OCH₃ | oil |
| O | O | (CH₂)₂ | OCH₂CH₃ | |
| O | O | (CH₂)₂ | OCH(CH₃)₂ | |
| O | O | CH(CH₃)CH₂ | OCH₃ | |
| O | O | (CH₂)₃ | OCH₃ | |
| O | O | (CH₂)₄ | OCH₃ | |
| O | O | (CH₂)₂ | Cl | oil |
| O | O | (CH₂)₂ | Br | |
| O | O | (CH₂)₂ | F | |
| O | O | CH(CH₃)CH₂ | Cl | |
| O | O | CH(CH₃)CH₂ | Br | |
| O | O | CH(CH₃)CH₂ | F | |
| O | O | (CH₂)₃ | Cl | |
| O | O | (CH₂)₃ | Br | |
| O | O | (CH₂)₃ | F | |
| O | O | (CH₂)₄ | Cl | |
| O | O | (CH₂)₄ | Br | |
| O | O | (CH₂)₄ | F | |
| S | S | (CH₂)₂ | OCH₃ | |
| S | S | (CH₂)₂ | OCH₂CH₃ | |
| S | S | (CH₂)₂ | OCH(CH₃)₂ | |
| S | S | CH(CH₃)CH₂ | OCH₃ | |
| S | S | (CH₂)₃ | OCH₃ | |
| S | S | (CH₂)₄ | OCH₃ | |
| S | S | (CH₂)₂ | Cl | |
| S | S | (CH₂)₂ | Br | |
| S | S | (CH₂)₂ | F | |
| S | S | CH(CH₃)CH₂ | Cl | |
| S | S | CH(CH₃)CH₂ | Br | |
| S | S | CH(CH₃)CH₂ | F | |
| S | S | (CH₂)₃ | Cl | |
| S | S | (CH₂)₃ | Br | |
| S | S | (CH₂)₃ | F | |
| S | S | (CH₂)₄ | Cl | |
| S | S | (CH₂)₄ | Br | |
| S | S | (CH₂)₄ | F | |
| O | S | (CH₂)₂ | OCH₃ | |
| O | S | (CH₂)₂ | OCH₂CH₃ | |
| O | S | (CH₂)₂ | OCH(CH₃)₂ | |
| O | S | CH(CH₃)CH₂ | OCH₃ | |
| O | S | (CH₂)₃ | OCH₃ | |

-continued

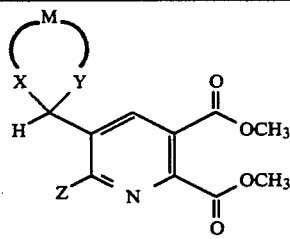

(V)

| X | Y | M | M | mp °C. |
|---|---|---|---|---|
| O | S | (CH₂)₄ | OCH₃ | |
| O | S | (CH₂)₂ | Cl | |
| O | S | (CH₂)₂ | Br | |
| O | S | (CH₂)₂ | F | |
| O | S | CH(CH₃)CH₂ | Cl | |
| O | S | CH(CH₃)CH₂ | Br | |
| O | S | CH(CH₃)CH₂ | F | |
| O | S | (CH₂)₃ | Cl | |
| O | S | (CH₂)₃ | Br | |
| O | S | (CH₂)₃ | F | |
| O | S | (CH₂)₄ | Cl | |
| O | S | (CH₂)₄ | Br | |
| O | S | (CH₂)₄ | F | |
| NCH₃ | O | (CH₂)₂ | H | oil |
| NCH₂CH₃ | O | (CH₂)₂ | H | |
| NCH₃ | O | (CH₂)₃ | H | |
| NCH₃ | O | (CH₂)₄ | H | |
| NCOCH₃ | O | (CH₂)₂ | H | oil |
| NCOCH₃ | O | (CH₂)₃ | H | |
| NCOCH₃ | O | (CH₂)₄ | H | |
| NCOCH₂CH₃ | O | (CH₂)₂ | H | |
| NCOCH(CH₃)₂ | O | (CH₂)₂ | H | oil |
| NCO₂CH₃ | O | (CH₂)₂ | H | oil |
| NCO₂CH₃ | O | CH(CH₃)CH₂ | H | |
| NCO₂CH₃ | O | (CH₂)₃ | H | |
| NCO₂CH₃ | O | (CH₂)₄ | H | |
| NCO₂CH₂CH₃ | O | (CH₂)₂ | H | oil |
| NCO₂CH(CH₃)₂ | O | (CH₂)₂ | H | |
| NCON(CH₃)₂ | O | (CH₂)₂ | H | oil |
| NCON(CH₃)₂ | O | (CH₂)₃ | H | |
| NCON(CH₃)₂ | O | (CH₂)₄ | H | |
| NCON(CH₂CH₃)₂ | O | (CH₂)₂ | H | |
| NCONHCH₃ | O | (CH₂)₂ | H | |
| NCONHCH₂CH₃ | O | (CH₂)₂ | H | |
| NCONHCH₂CH₂CH₃ | O | (CH₂)₂ | H | |
| NCONHCH(CH₃)₂ | O | (CH₂)₂ | H | oil |
| NCO₂CH₂CH₃ | O | (CH₂)₃ | H | oil |
| NCO₂CH₂CH₃ | O | (CH₂)₄ | H | |
| NCH₃ | NCOCH₃ | COCH₂ | H | |
| NCH₃ | NCO₂CH₃ | COCH₂ | H | |
| NCH₃ | NCON(CH₃)₂ | COCH₂ | H | |
| NCH₂CH₃ | NCOCH₃ | COCH₂ | H | |
| NCH₂CH₃ | NCO₂CH₃ | COCH₂ | H | |
| NCH₂CH₃ | NCO₂CH₃ | COCH₂ | H | |
| O | NCOCH₃ | COCH₂ | H | |
| O | NCOCH₂CH₃ | COCH₂ | H | |
| O | NCO₂CH₃ | COCH₂ | H | |
| O | NCO₂CH₂CH₃ | COCH₂ | H | |
| O | NCON(CH₃)₂ | COCH₂ | H | |
| O | NCON(CH₂CH₃)₂ | COCH₂ | H | |
| NCH₃ | NCOCH₃ | COCH(CH₃) | H | |
| NCH₃ | NCO₂CH₃ | COCH(CH₃) | H | |
| NCH₃ | NCON(CH₃)₂ | COCH(CH₃) | H | |
| O | NCOCH₃ | COCH(CH₃) | H | |
| O | NCO₂CH₃ | COCH(CH₃) | H | |
| O | NCON(CH₃)₂ | COCH(CH₃) | H | |
| NCH₃ | O | COCH₂ | H | |
| NCH₃ | O | COCH₂CH₂ | H | |
| NCH₃ | O | COCH(CH₃) | H | |
| NCH₃ | NCH₃ | COCO | H | |
| NCH₃ | NCH₃ | COCH₂CO | H | |
| NCH₃ | O | COCO | H | |
| NCH₃ | O | COCH₂CO | H | |
| NCH₃ | NCH₃ | — | CH₃ | |
| NCH₂CH₃ | NCH₃ | — | CH₃ | |
| NCH₂CH₃ | NCH₂CH₃ | — | CH₃ | |
| NCH₃ | NH | (CH₂)₂ | CH₃ | |

-continued

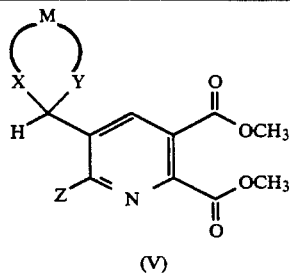

(V)

| X | Y | M | M | mp °C. |
|---|---|---|---|---|
| NCH₃ | NCOCH₃ | (CH₂)₂ | CH₃ | |
| NCH₃ | NCOCH₂CH₃ | (CH₂)₂ | CH₃ | |
| NCH₃ | NCOCH₃ | (CH₂)₃ | CH₃ | |
| NCH₃ | NCO₂CH₃ | (CH₂)₂ | CH₃ | |
| NCH₃ | NCO₂CH₃ | (CH₂)₃ | CH₃ | |
| NCH₃ | NCOCH₃ | (CH₂)₃ | CH₃ | |
| NCH₃ | NCOCH₃ | (CH₂)₄ | CH₃ | |
| NCH₃ | S | (CH₂)₂ | CH₃ | |
| NCH₃ | S | (CH₂)₃ | CH₃ | |
| NCH₃ | S | (CH₂)₄ | CH₃ | |
| NCOCH₃ | S | (CH₂)₂ | CH₃ | |
| NCO₂CH₃ | S | (CH₂)₃ | CH₃ | |
| NCH₃ | NCH₃ | — | H | |
| NCH₂CH₃ | NCH₃ | — | H | |
| NCH₂CH₃ | NCH₂CH₃ | — | H | |
| NCH₃ | NH | (CH₂)₂ | H | |
| NCH₃ | NCOCH₃ | (CH₂)₂ | H | |
| NCH₃ | NCOCH₂CH₃ | (CH₂)₂ | H | |
| NCH₃ | NCOCH₃ | (CH₂)₃ | H | |
| NCH₃ | NCO₂CH₃ | (CH₂)₂ | H | |
| NCH₃ | NCO₂CH₃ | (CH₂)₃ | H | |
| NCH₃ | NCOCH₃ | (CH₂)₃ | H | |
| NCH₃ | NCO₂CH₃ | (CH₂)₄ | H | |
| NCH₃ | NCOCH₃ | (CH₂)₄ | H | |
| NCH₃ | S | (CH₂)₂ | H | |
| NCH₃ | S | (CH₂)₃ | H | |
| NCH₃ | S | (CH₂)₄ | H | |
| NCOCH₃ | S | (CH₂)₂ | H | |
| NCO₂CH₃ | S | (CH₂)₃ | H | |
| O | O | COCH₂ | H | |
| O | O | COCH₂CH₂ | H | |
| O | O | COCH₂CH(CH₃) | H | |
| O | O | COCO | H | |
| O | O | COCH₂CO | H | |
| O | O | COCH=CH | H | |
| O | O | COCH=C(CH₃) | H | |
| O | O | CH=CH | H | |
| O | O | CH=CHCH₂ | H | |
| O | O | (CH₃)C=CHCH₂ | H | |
| O | O | CH=CHCH(CH₃) | H | |
| O | S | COCH₂ | H | |
| O | O | CH₂CH(CO₂CH₃) | H | |

EXAMPLE 20

Preparation of
5-(1,3-Dioxolan-2-yl)-2,3-pyridinedicarboxylic acid

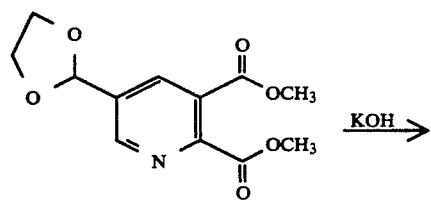 $\xrightarrow{\text{KOH}}$

-continued

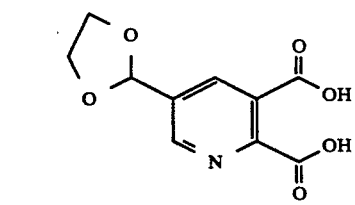

5-(1,3-Dioxolan-2-yl)-2,3-pyridinedicarboxylic acid, dimethyl ester (2.86 g, 0.011 mol) in methanol is added dropwise to a mixture of potassium hydroxide (1.26 g, 0.022 mol) and methanol. The reaction mixture is heated for 3 hours and 30 minutes at about 62° C., cooled to room temperature, acidified to pH 1 with concentrated hydrochloric acid, filtered through diatomaceous earth and the filtrate is concentrated in vacuo to yield the title compound as a pale yellow powder (2.86 g, 100%), identified by IR and NMR spectral analyses.

EXAMPLE 21

Preparation of 5-(1,3-Dioxolan-2-yl)-2,3-pyridinedicarboxylic acid

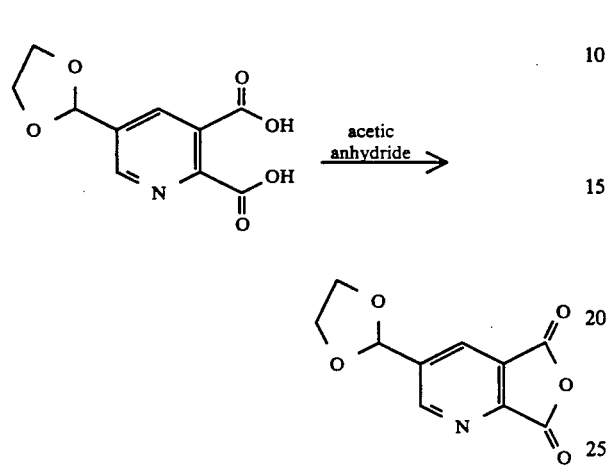

A solution of 5-(1,3-dioxolan-2-yl)-2,3-pyridinedicarboxylic acid (2.86 g, 0.012 mol), acetic anhydride (11.3 mL, 0.12 mol) and pyridine is stirred at room temperature for 1 hour and 45 minutes, then at reflux temperature for 4 hours. The reaction mixture is concentrated in vacuo to give the title compound as an oil (2.64 g, 100%), identified by IR spectra analysis.

EXAMPLE 22

Preparation of 2-[(1-Carbamoyl-1,2-dimethylpropyl)-carbamoyl]-5-(1,3-dioxolan-2-yl)nicotinic acid

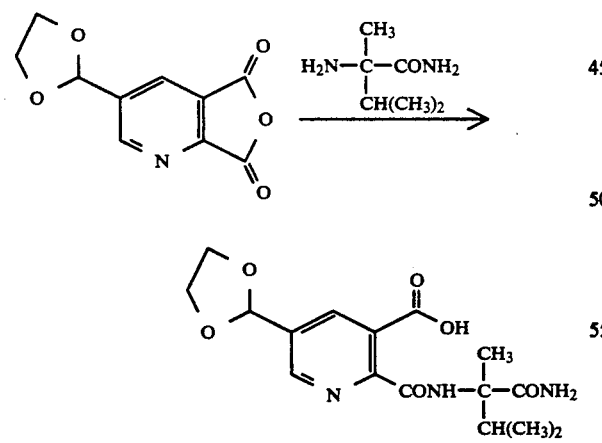

A solution of 5-(1,3-dioxolan-2-yl)-2,3-pyridinedicarboxylic anhydride (2.64 g, 0.012 mol) and 2-amino-2,3-dimethylbutyramide (1.55 g, 0.012 mol) in tetrahydrofuran is stirred for 2 days at room temperature. The reaction mixture is concentrated in vacuo to give the title compound as an orange oil (5.4 g, 100%), identified by NMR spectra analysis.

EXAMPLE 23

Preparation of 5-(1,3-Dioxolan-2-yl)-2-(4-isopropyl-4-methyl-5-oxo-2-imidazolin-2-yl)nicotinic acid

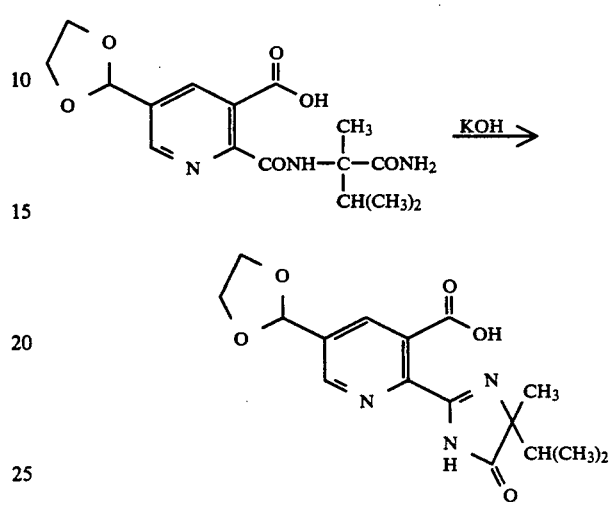

2-[(1-Carbamoyl-1,2-dimethylpropyl)carbamoyl]-5-(1,3-dioxolan-2-yl)nicotinic acid (4.19 g, 0.019 mol) and 15% potassium hydroxide is heated at 80° C. for 1 hour. The reaction mixture is acidified to pH 3 with concentrated hydrochloric acid and methylene chloride is added. The methylene chloride layer is separated, dried over anhydrous magnesium sulfate and concentrated in vacuo to give an oil. The oil is chromatographed using silica gel and methylene chloride with increasing percentage of ether as eluent to give the title compound as a pale yellow solid (0.19 g, 5%), mp 156° C., identified by IR and NMR spectral analyses.

EXAMPLE 24

Preparation of 5-(4-Methyl-1,3-dioxolan-2-yl)-2 (4-ispopropyl-4-methyl-5-oxo-2-imidazolin-2-yl)nicotinic acid

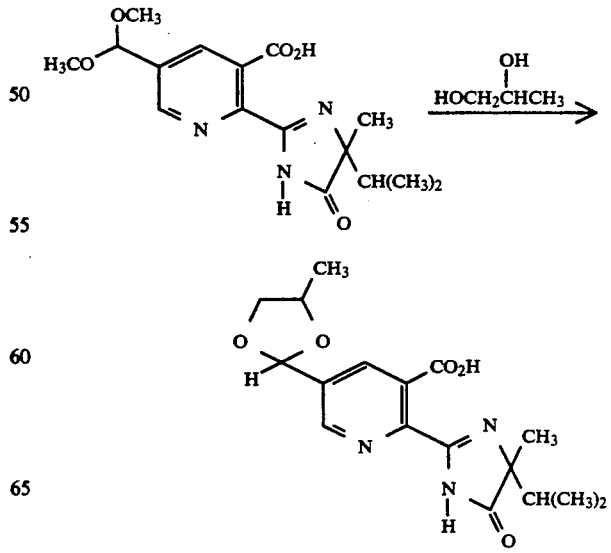

A solution of 5-formyl-2-(4-isopropyl-4-methyl-5-oxo-2-imidazolin-2-yl)nicotinic acid, 5-(dimethyl acetal) (0.65 g, 0.00194 mol), 1,2-propanediol (0.65 g, 0.0085 mol) and a catalytic amount of p-toluenesulfonic acid in toluene is heated at reflux temperature for 2 hours. The reaction mixture is cooled to room temperature, concentrated in vacuo and the residue is dissolved in methylene chloride. The methylene chloride solution is washed sequentially with water and brine, dried over anhydrous magnesium sulfate and concentrated in vacuo to give a solid. The solid is chromatographed using silica gel and a gradient elution of 100% methylene chloride to 5% methanol in methylene chloride to yield the title compound as a yellow solid (0 5 g, 74%), mp 50°-62° C., identified by IR and NMR spectral analyses.

EXAMPLE 25

Preparation of 2-(4-Isopropyl-4-methyl-5-oxo-2-imidazolin-2-yl)-5-(3-methyl-2-oxazolidinyl)nicotinic acid, compound with 2-(methylamino)

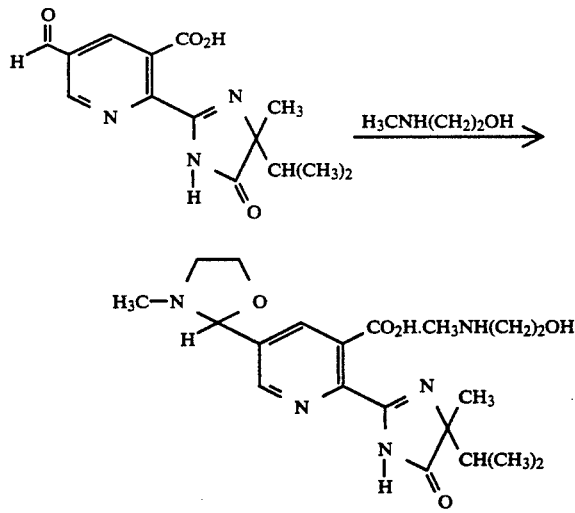

A solution of 5-formyl-2-(4-isopropyl-4-methyl-5-oxo-2-imidazolin-2-yl)nicotinic acid (0.36 g, 0.00125 mol) and 2-(methylamino)ethanol (0.19 g, 0.0025 mol) in chloroform is heated for 2 hours and 30 minutes at reflux temperature. The reaction mixture is then concentrated in vacuo at aspirator pressure to give the title compound as a yellow gum (0.40 g, 76%), identified by IR and NMR spectral analyses.

EXAMPLE 26

Preparation of 5-m-Dioxan-2-yl)-2-(4-isopropyl-4-methyl-5-oxo-2-imidazolin-2-yl)nicotinic acid

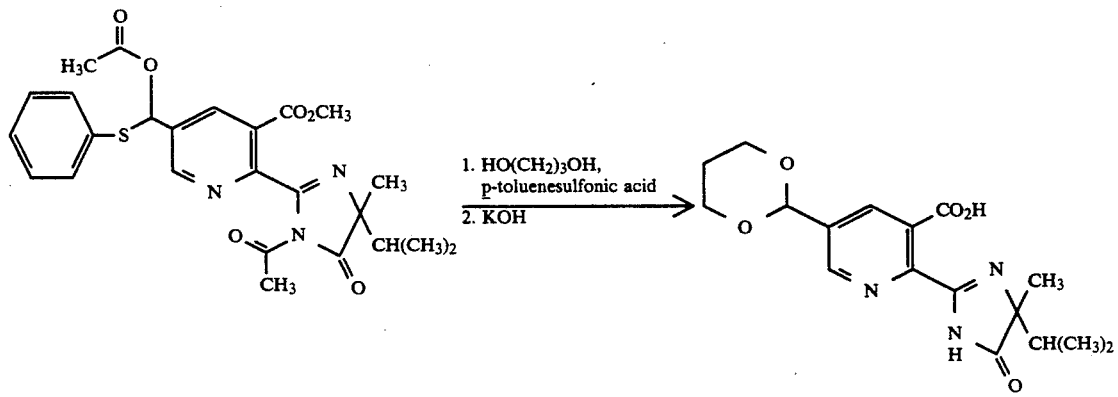

A solution of 2-(1-acetyl-4-isopropyl-4-methyl-5-oxo-2-imidazolin-2-yl)-5-[hydroxy(phenylthio)methyl]nicotinic acid, methyl ester, 5-acetate (0.48 g, 0.00096 mol), a catalytic amount of p-toluenesulfonic acid, 1,3-propanediol and toluene is heated at reflux temperatures for 3 hours. Concentration in vacuo yields an oil which is dissolved into methylene chloride, washed with 5% sodium bicarbonate solution, dried over anhydrous magnesium sulfate and concentrated in vacuo to yield an oil. The oil is dissolved into tetrahydrofuran and 1 molar potassium hydroxide is added and the reaction mixture is stirred at 0° C. for 30 minutes, then at room temperature for 2 hours. Concentration in vacuo gives an oil to which water is added and the pH is adjusted to 3.0 with concentrated hydrochloric acid. The aqueous solution is saturated with sodium chloride and extracted with methylene chloride. The combined methylene chloride extracts are dried over anhydrous magnesium sulfate and concentrated in vacuo to give an oil The oil is chromatographed using silica gel and 100% methylene chloride to 10% methanol in methylene chloride as eluant to give the title compound as a yellow solid (0.2 g, 60%), mp 188°-196° C., identified by IR and NMR spectral analyses.

Using the above procedure and substituting 2,2-dimethyl-1,3-propanediol gives 5-(5,5-dimethyl-m-dioxan-2-yl)-2-(4-isopropyl-4-methyl-5-oxo-2-imidazolin-2-yl)nicotinic acid, mp 163°-170° C., identified by IR and NMR spectral analyses.

EXAMPLE 27

Preparation of 5-(1,3-Dioxepan-2-yl)-2-(4-isopropyl-4-methyl-5-oxo-2-imidazolin-2-yl)nicotinic acid -continued

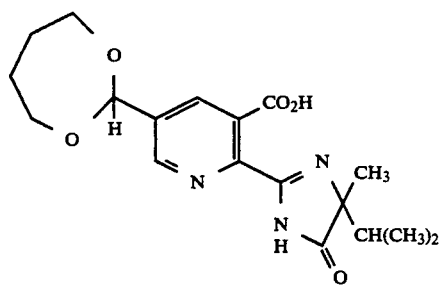

5-(1,3-Dioxepan-2-yl)-2,3-pyridinedicarboxylic acid, dimethyl ester (0.9 g, 0.00305 mol) in toluene is added to 2-amino-2,3-dimethylbutyramide (0.4 g, 0.00305 mol) and potassium tert-butoxide (0.69 g, 0.0061 mol) in toluene. The mixture is heated for 3 hours from 60° to 70° C. The reaction mixture is cooled to room temperature, water is added and the mixture is concentrated in vacuo to give an oil. The oil is diluted with water and washed with ether. The aqueous solution is acidified to pH 3.1 with 2 normal hydrochloric acid solution and extracted with methylene chloride. The combined methylene chloride extracts are dried over anhydrous magnesium sulfate and concentrated in vacuo to give the title compound as a white solid (0.63 g, 57%) mp 60°-69° C., identified by IR and NMR spectral analyses.

Following the above procedure and substituting the appropriately substituted 2,3-pyridinedicarboxylic acid, dimethyl ester, the following compounds are obtained.

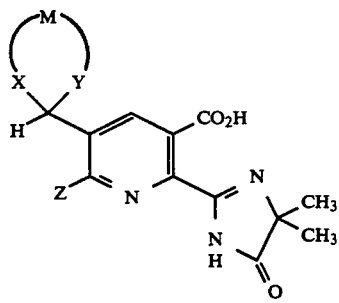

| X | Y | M | Z | mp °C. |
|---|---|---|---|---|
| O | O | (CH$_2$)$_4$ | H | 60-69 |
| S | O | (CH$_2$)$_2$ | H | 72-76 |
| NCH$_3$ | NCH$_3$ | — | H | 174-176 |
| O | O | (CH$_2$)$_2$ | CH$_3$ | 75 |
| O | O | (CH$_2$)$_3$ | OCH$_3$ | 222-223 |
| O | O | (CH$_2$)$_2$ | Cl | 79-80 |
| S | S | (CH$_2$)$_2$ | H | 125-133 |
| O | NCO$_2$CH$_3$ | (CH$_2$)$_2$ | H | 178-180 |
| O | NCO$_2$CH$_2$CH$_3$ | (CH$_2$)$_2$ | H | 75-77 |
| O | NCOCH$_3$ | (CH$_2$)$_2$ | H | 167-168 |
| O | NCON(CH$_3$)$_2$ | (CH$_2$)$_2$ | H | 198-199 |
| O | NCOCH(CH$_3$)$_2$ | (CH$_2$)$_2$ | H | 91-93 |
| O | NCONHCH(CH$_3$)$_2$ | (CH$_2$)$_2$ | H | 181-183 |
| O | NCO$_2$CH$_2$CH$_3$ | (CH$_2$)$_3$ | H | 77-79 |
| O | NSO$_2$CH$_3$ | (CH$_2$)$_3$ | H | 188-192 |

EXAMPLE 28

Preparation of 5-(1-Acetyl-3-methyl-2-imidazolidinyl)-2-(4-isopropyl-4-methyl-5-oxo-2-imidazolin-2-yl)nicotinic acid ammonium salt

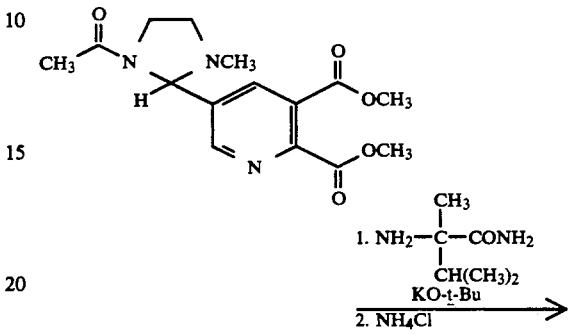

To a stirred solution of dimethyl 5-(1-acetyl-3-methyl-2-imidazolidinyl)pyridine-2,3-dicarboxylate (0.70 g, 0.0022 mol), and 2-amino-2,3-dimethylbutyramide (0.28 g, 0.0022 mol) in toluene (10 mL) is added potassium tert-butoxide (0.49 g, 0.0044 mol). The resulting mixture is stirred for 2 hours at 80° C. to 90° C. After cooling to room temperature, the reaction is quenched by the addition of water (15 mL) and ammonium chloride (0.25 g). The layers are separated, the aqueous solution concentrated under high vacumn, the product triturated with 33% ethanol in chloroform and filtered. The filtrate is concentrated in vacuo to afford the title compound (0.95 g, 100%) as a gold solid, mp 93°-98° C., identified by IR and NMR spectral analyses.

EXAMPLE 29

Preparation of Methyl 2-(4-Isopropyl-4-methyl-5-oxo-2-imidazolin-2-yl)-5-(4-methyl-6-oxo-1,3-dioxan-2-yl)-nicotinate

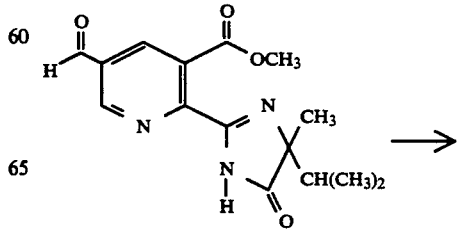

-continued

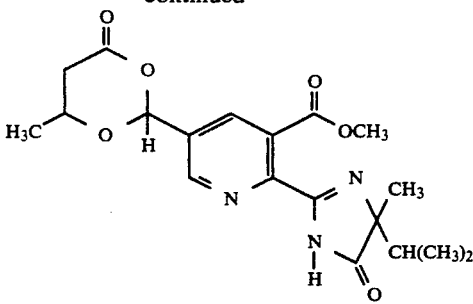

A solution of methyl 5-formyl-2-(4-isopropyl-4-methyl-5-oxo-2-imidazolin-2-yl)nicotinate (0.55 g, 0.0018 mol), 3-hydroxybutyric acid (0.28 g, 0.0027 mol) and a catalytic amount of para-toluenesulfonic acid in chloroform (25 mL) is heated at reflux temperature for 113 hours. During this time, water is removed by placement of an addition funnel containing 3 angstrom molecular sieves between the reaction flask and the reflux condensor. The reaction mixture is poured into aqueous saturated sodium bicarbonate and the layers are separated. The aqueous portion is extracted with additional methylene chloride and the combined organic extracts are dried over anhydrous magnesium sulfate and concentrated in vacuo to give a residue. The residue is purified by chromatography using silica gel and ethyl acetate in hexanes as eluant to yield the title compound (0.14 g, 20%) as a white solid, mp 65°–75° C., identified by IR and NMR spectral analyses.

Formula I compounds that may be prepared using the above-described procedure are listed below.

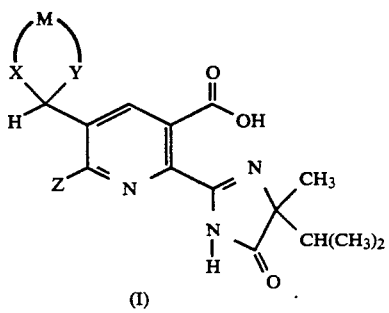

(I)

| X | Y | M | Z | mp °C. |
|---|---|---|---|---|
| O | O | $(CH_2)_2$ | H | 156 |
| O | O | $CH(CH_3)CH_2$ | H | 50–62 |
| O | O | $C(CH_3)_2CH_2$ | H | |
| O | O | $CH(CH_3)CH(CH_3)$ | H | |
| O | O | $(CH_2)_3$ | H | 188–196 |
| O | O | $CH(CH_3)CH_2CH_2$ | H | |
| O | O | $CH_2CH(CH_3)CH_2$ | H | |
| O | O | $C(CH_3)_2CH_2CH_2$ | H | |
| O | O | $CH(CH_3)CH—(CH_3)CH_2$ | H | |
| O | O | $CH(CH_3)CH_2CH(CH_3)$ | H | |
| O | O | $CH_2C(CH_3)_2CH_2$ | H | 163–170 |
| O | O | $(CH_2)_4$ | H | 60–69 |
| O | O | $CH(CH_3)CH_2CH_2CH_2$ | H | |
| O | O | $CH_2CH(CH_3)CH_2CH_2$ | H | |
| O | O | $C(CH_3)_2CH_2CH_2CH_2$ | H | |
| O | O | $CH(CH_3)CH(CH_3)—CH_2CH_2$ | H | |
| O | O | $CH(CH_3)CH_2—CH(CH_3)CH_2$ | H | |
| O | O | $CH(CH_3)CH_2—CH_2CH(CH_3)$ | H | |
| O | O | $CH_2C(CH_3)_2—CH_2CH_2$ | H | |
| O | O | $CH_2CH(CH_3)—CH(CH_3)CH_2$ | H | |
| O | O | $(CH_2)_5$ | H | |
| O | O | $CH_2CH_2OCH_2—CH_2$ | H | |
| O | O | $CH_2CH_2SCH_2—CH_2$ | H | |
| O | S | $(CH_2)_2$ | H | 72–76 |
| O | S | $CH(CH_3)CH_2$ | H | |
| O | S | $C(CH_3)_2CH_2$ | H | |
| O | S | $CH(CH_3)CH(CH_3)$ | H | |
| O | S | $(CH_2)_3$ | H | |
| O | S | $CH(CH_3)CH_2CH_2$ | H | |
| O | S | $CH_2CH(CH_3)CH_2$ | H | |
| O | S | $C(CH_3)_2CH_2CH_2$ | H | |
| O | S | $CH(CH_3)CH—(CH_3)CH_2$ | H | |
| O | S | $CH(CH_3)CH_2—CH(CH_3)$ | H | |
| O | S | $CH_2C(CH_3)_2—CH_2$ | H | |
| O | S | $(CH_2)_4$ | H | |
| O | S | $CH(CH_3)CH_2—CH_2CH_2$ | H | |
| O | S | $CH_2CH(CH_3)—CH_2CH_2$ | H | |
| O | S | $C(CH_3)_2CH_2—CH_2CH_2$ | H | |
| O | S | $CH(CH_3)CH(CH_3)—CH_2CH_2$ | H | |
| O | S | $CH(CH_3)CH_2CH—(CH_3)CH_2$ | H | |
| O | S | $CH(CH_3)CH_2CH_2—CH(CH_3)$ | H | |
| O | S | $CH_2C(CH_3)_2—CH_2CH_2$ | H | |
| O | S | $CH_2CH(CH_3)—CH(CH_3)CH_2$ | H | |
| O | S | $(CH_2)_5$ | H | |

-continued

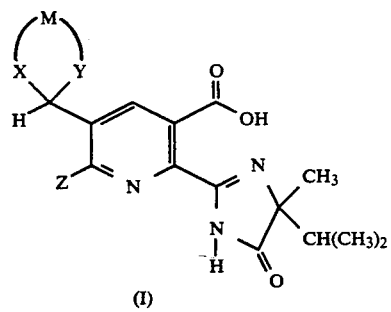
(I)

| X | Y | M | Z | mp °C. |
|---|---|---|---|---|
| O | S | CH₂CH₂OCH₂CH₂ | H | |
| O | S | CH₂CH₂SCH₂CH₂ | H | |
| S | S | (CH₂)₂ | H | 125–133 |
| S | S | CH(CH₃)CH₂ | H | |
| S | S | C(CH₃)₂CH₂ | H | |
| S | S | CH(CH₃)CH(CH₃) | H | |
| S | S | (CH₂)₃ | H | |
| S | S | CH(CH₃)CH₂CH₂ | H | |
| S | S | CH₂CH(CH₃)CH₂ | H | |
| S | S | C(CH₃)₂CH₂CH₂ | H | |
| S | S | CH(CH₃)CH(CH₃)—CH₂ | H | |
| S | S | CH(CH₃)CH₂CH(CH₃) | H | |
| S | S | CH₂C(CH₃)₂CH₂ | H | |
| S | S | (CH₂)₄ | H | |
| S | S | CH(CH₃)CH₂CH₂CH₂ | H | |
| S | S | CH₂CH(CH₃)CH₂CH₂ | H | |
| S | S | C(CH₃)₂CH₂CH₂CH₂ | H | |
| S | S | CH(CH₃)CH(CH₃)—CH₂CH₂ | H | |
| S | S | CH(CH₃)CH—(CH₃)CH₂ | H | |
| S | S | CH(CH₃)CH₂—CH(CH₃)CH₂ | H | |
| S | S | CH(CH₃)CH₂—CH₂CH(CH₃) | H | |
| S | S | CH₂C(CH₃)₂—CH₂CH₂ | H | |
| S | S | CH₂CH(CH₃)—CH(CH₃)CH₂ | H | |
| S | S | (CH₂)₅ | H | |
| S | S | CH₂CH₂OCH₂CH₂ | H | |
| S | S | CH₂CH₂SCH₂CH₂ | H | |
| O | O | (CH₂)₂ | CH₃ | 75 |
| O | O | (CH₂)₂ | CH₂CH₃ | |
| O | O | (CH₂)₂ | CH(CH₃)₂ | |
| O | O | (CH₂)₂ | CH₂CH₂CH₃ | |
| O | O | CH(CH₃)CH₂ | CH₃ | |
| O | O | C(CH₃)₂CH₂ | CH₃ | |
| O | O | (CH₂)₃ | CH₃ | |
| O | O | (CH₂)₄ | CH₃ | |
| O | S | (CH₂)₂ | CH₃ | |
| O | S | (CH₂)₂ | CH₂CH₃ | |
| O | S | (CH₂)₂ | CH(CH₃)₂ | |
| O | S | (CH₂)₂ | CH₂CH₂CH₃ | |
| O | S | CH(CH₃)CH₂ | CH₃ | |
| O | S | C(CH₃)₂CH₂ | CH₃ | |
| O | S | (CH₂)₃ | CH₃ | |
| O | S | (CH₂)₄ | CH₃ | |
| S | S | (CH₂)₂ | CH₃ | |
| S | S | (CH₂)₂ | CH₂CH₃ | |
| S | S | (CH₂)₂ | CH(CH₃)₂ | |
| S | S | (CH₂)₂ | CH₂CH₂CH₃ | |
| S | S | CH(CH₃)CH₂ | CH₃ | |
| S | S | C(CH₃)₂CH₂ | CH₃ | |
| S | S | (CH₂)₃ | CH₃ | |
| S | S | (CH₂)₄ | CH₃ | |
| O | O | (CH₂)₂ | OCH₃ | 222–223 |
| O | O | (CH₂)₂ | OCH₂CH₃ | |
| O | O | (CH₂)₂ | OCH(CH₃)₂ | |
| O | O | CH(CH₃)CH₂ | OCH₃ | |
| O | O | (CH₂)₃ | OCH₃ | |
| O | O | (CH₂)₄ | OCH₃ | |
| O | O | (CH₂)₂ | Cl | 79–80 |
| O | O | (CH₂)₂ | Br | |
| O | O | (CH₂)₂ | F | |
| O | O | CH(CH₃)CH₂ | Cl | |
| O | O | CH(CH₃)CH₂ | Br | |
| O | O | CH(CH₃)CH₂ | F | |
| O | O | (CH₂)₃ | Cl | |
| O | O | (CH₂)₃ | Br | |
| O | O | (CH₂)₃ | F | |

-continued

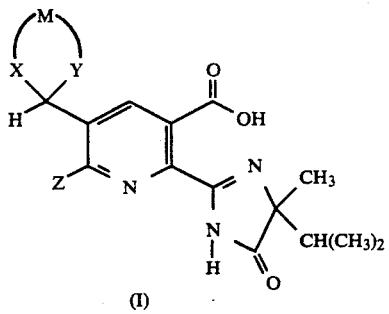

(I)

| X | Y | M | Z | mp °C. |
|---|---|---|---|---|
| O | O | (CH$_2$)$_4$ | Cl | |
| O | O | (CH$_2$)$_4$ | Br | |
| O | O | (CH$_2$)$_4$ | F | |
| S | S | (CH$_2$)$_2$ | OCH$_3$ | |
| S | S | (CH$_2$)$_2$ | OCH$_2$CH$_3$ | |
| S | S | (CH$_2$)$_2$ | OCH(CH$_3$)$_2$ | |
| S | S | CH(CH$_3$)CH$_2$ | OCH$_3$ | |
| S | S | (CH$_2$)$_3$ | OCH$_3$ | |
| S | S | (CH$_2$)$_4$ | OCH$_3$ | |
| S | S | (CH$_2$)$_2$ | Cl | |
| S | S | (CH$_2$)$_2$ | Br | |
| S | S | (CH$_2$)$_2$ | F | |
| S | S | CH(CH$_3$)CH$_2$ | Cl | |
| S | S | CH(CH$_3$)CH$_2$ | Br | |
| S | S | CH(CH$_3$)CH$_2$ | F | |
| S | S | (CH$_2$)$_3$ | Cl | |
| S | S | (CH$_2$)$_3$ | Br | |
| S | S | (CH$_2$)$_3$ | F | |
| S | S | (CH$_2$)$_4$ | Cl | |
| S | S | (CH$_2$)$_4$ | Br | |
| S | S | (CH$_2$)$_4$ | F | |
| O | S | (CH$_2$)$_2$ | OCH$_3$ | |
| O | S | (CH$_2$)$_2$ | OCH$_2$CH$_3$ | |
| O | S | (CH$_2$)$_2$ | OCH(CH$_3$)$_2$ | |
| O | S | CH(CH$_3$)CH$_2$ | OCH$_3$ | |
| O | S | (CH$_2$)$_3$ | OCH$_3$ | |
| O | S | (CH$_2$)$_4$ | OCH$_3$ | |
| O | S | (CH$_2$)$_2$ | Cl | |
| O | S | (CH$_2$)$_2$ | Br | |
| O | S | (CH$_2$)$_2$ | F | |
| O | S | CH(CH$_3$)CH$_2$ | Cl | |
| O | S | CH(CH$_3$)CH$_2$ | Br | |
| O | S | CH(CH$_3$)CH$_2$ | F | |
| O | S | (CH$_2$)$_3$ | Cl | |
| O | S | (CH$_2$)$_3$ | Br | |
| O | S | (CH$_2$)$_3$ | F | |
| O | S | (CH$_2$)$_4$ | Cl | |
| O | S | (CH$_2$)$_4$ | Br | |
| O | S | (CH$_2$)$_4$ | F | |
| NCH$_3$ | O | (CH$_2$)$_2$ | H | oil |
| NCH$_2$CH$_3$ | O | (CH$_2$)$_2$ | H | |
| NCH$_3$ | O | (CH$_2$)$_3$ | H | |
| NCH$_3$ | O | (CH$_2$)$_4$ | H | |
| NCOCH$_3$ | O | (CH$_2$)$_2$ | H | 167–168 |
| NCOCH$_3$ | O | (CH$_2$)$_3$ | H | |
| NCOCH$_3$ | O | (CH$_2$)$_4$ | H | |
| NCOCH$_2$CH$_3$ | O | (CH$_2$)$_2$ | H | |
| NCOCH(CH$_3$)$_2$ | O | (CH$_2$)$_2$ | H | 91–93 |
| NCO$_2$CH$_3$ | O | (CH$_2$)$_2$ | H | 178–180 |
| NCO$_2$CH$_3$ | O | CH(CH$_3$)CH$_2$ | H | |
| NCO$_2$CH$_3$ | O | (CH$_2$)$_3$ | H | |
| NCO$_2$CH$_3$ | O | (CH$_2$)$_4$ | H | |
| NCO$_2$CH$_2$CH$_3$ | O | (CH$_2$)$_2$ | H | 75–77 |
| NCO$_2$CH(CH$_3$)$_2$ | O | (CH$_2$)$_2$ | H | |
| NCON(CH$_3$)$_2$ | O | (CH$_2$)$_2$ | H | 198–199 |
| NCON(CH$_3$)$_2$ | O | (CH$_2$)$_3$ | H | |
| NCON(CH$_3$)$_2$ | O | (CH$_2$)$_4$ | H | |
| NCON(CH$_2$CH$_3$)$_2$ | O | (CH$_2$)$_2$ | H | |
| NCONHCH$_3$ | O | (CH$_2$)$_2$ | H | |
| NCONHCH$_2$CH$_3$ | O | (CH$_2$)$_2$ | H | |
| NCONHCH$_2$CH$_2$CH$_3$ | O | (CH$_2$)$_2$ | H | |
| NCONHCH(CH$_3$)$_2$ | O | (CH$_2$)$_2$ | H | 181–183 |
| NCO$_2$CH$_2$CH$_3$ | O | (CH$_2$)$_3$ | H | 77–79 |
| NCO$_2$CH$_2$CH$_3$ | O | (CH$_2$)$_4$ | H | |
| NCH$_3$ | NCOCH$_3$ | COCH$_2$ | H | |

-continued

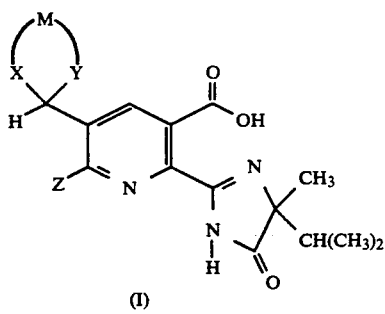

(I)

| X | Y | M | Z | mp °C. |
|---|---|---|---|---|
| NCH$_3$ | NCO$_2$CH$_3$ | COCH$_2$ | H | |
| NCH$_3$ | NCON(CH$_3$)$_2$ | COCH$_2$ | H | |
| NCH$_2$CH$_3$ | NCOCH$_3$ | COCH$_2$ | H | |
| NCH$_2$CH$_3$ | NCO$_2$CH$_3$ | COCH$_2$ | H | |
| NCH$_2$CH$_3$ | NCO$_2$CH$_3$ | COCH$_2$ | H | |
| O | NCOCH$_3$ | COCH$_2$ | H | |
| O | NCOCH$_2$CH$_3$ | COCH$_2$ | H | |
| O | NCO$_2$CH$_3$ | COCH$_2$ | H | |
| O | NCO$_2$CH$_2$CH$_3$ | COCH$_2$ | H | |
| O | NCON(CH$_3$)$_2$ | COCH$_2$ | H | |
| O | NCON(CH$_2$CH$_3$)$_2$ | COCH$_2$ | H | |
| NCH$_3$ | NCOCH$_3$ | COCH(CH$_3$) | H | |
| NCH$_3$ | NCO$_2$CH$_3$ | COCH(CH$_3$) | H | |
| NCH$_3$ | NCON(CH$_3$)$_2$ | COCH(CH$_3$) | H | |
| O | NCOCH$_3$ | COCH(CH$_3$) | H | |
| O | NCO$_2$CH$_3$ | COCH(CH$_3$) | H | |
| O | NCON(CH$_3$)$_2$ | COCH(CH$_3$) | H | |
| NCH$_3$ | O | COCH$_2$ | H | |
| NCH$_3$ | O | COCH$_2$CH$_2$ | H | |
| NCH$_3$ | O | COCH(CH$_3$) | H | |
| NCH$_3$ | NCH$_3$ | COCO | H | |
| NCH$_3$ | NCH$_3$ | COCH$_2$CO | H | |
| NCH$_3$ | O | COCO | H | |
| NCH$_3$ | O | COCH$_2$CO | H | |
| NCH$_3$ | NCH$_3$ | — | CH$_3$ | |
| NCH$_2$CH$_3$ | NCH$_3$ | — | CH$_3$ | |
| NCH$_2$CH$_3$ | NCH$_2$CH$_3$ | — | CH$_3$ | |
| NCH$_3$ | NH | (CH$_2$)$_2$ | CH$_3$ | |
| NCH$_3$ | NCOCH$_3$ | (CH$_2$)$_2$ | CH$_3$ | |
| NCH$_3$ | NCOCH$_2$CH$_3$ | (CH$_2$)$_2$ | CH$_3$ | |
| NCH$_3$ | NCOCH$_3$ | (CH$_2$)$_3$ | CH$_3$ | |
| NCH$_3$ | NCO$_2$CH$_3$ | (CH$_2$)$_2$ | CH$_3$ | |
| NCH$_3$ | NCO$_2$CH$_3$ | (CH$_2$)$_3$ | CH$_3$ | |
| NCH$_3$ | NCO$_2$CH$_3$ | (CH$_2$)$_4$ | CH$_3$ | |
| NCH$_3$ | NCOCH$_3$ | (CH$_2$)$_4$ | CH$_3$ | |
| NCH$_3$ | S | (CH$_2$)$_2$ | CH$_3$ | |
| NCH$_3$ | S | (CH$_2$)$_3$ | CH$_3$ | |
| NCH$_3$ | S | (CH$_2$)$_4$ | CH$_3$ | |
| NCOCH$_3$ | S | (CH$_2$)$_2$ | CH$_3$ | |
| NCO$_2$CH$_3$ | S | (CH$_2$)$_3$ | CH$_3$ | |
| NCH$_3$ | NCH$_3$ | — | H | 174–176 |
| NCH$_2$CH$_3$ | NCH$_3$ | — | H | |
| NCH$_2$CH$_3$ | NCH$_2$CH$_3$ | — | H | |
| NCH$_3$ | NH | (CH$_2$)$_2$ | H | |
| NCH$_3$ | NCOCH$_3$ | (CH$_2$)$_2$ | H | |
| NCH$_3$ | NCOCH$_2$CH$_3$ | (CH$_2$)$_2$ | H | |
| NCH$_3$ | NCOCH$_3$ | (CH$_2$)$_3$ | H | |
| NCH$_3$ | NCO$_2$CH$_3$ | (CH$_2$)$_2$ | H | |
| NCH$_3$ | NCO$_2$CH$_3$ | (CH$_2$)$_3$ | H | |
| NCH$_3$ | NCOCH$_3$ | (CH$_2$)$_3$ | H | |
| NCH$_3$ | NCO$_2$CH$_3$ | (CH$_2$)$_4$ | H | |
| NCH$_3$ | NCOCH$_3$ | (CH$_2$)$_4$ | H | |
| NCH$_3$ | S | (CH$_2$)$_2$ | H | |
| NCH$_3$ | S | (CH$_2$)$_3$ | H | |
| NCH$_3$ | S | (CH$_2$)$_4$ | H | |
| NCOCH$_3$ | S | (CH$_2$)$_2$ | H | |
| NCO$_2$CH$_3$ | S | (CH$_2$)$_3$ | H | |
| O | O | COCH$_2$ | H | |
| O | O | COCH$_2$CH$_2$ | H | |
| O | O | COCH$_2$CH(CH$_3$) | H | |
| O | O | COCO | H | |
| O | O | COCH$_2$CO | H | |
| O | O | COCH=CH | H | |
| O | O | COCH=C(CH$_3$) | H | |
| O | O | CH=CH | H | |

-continued

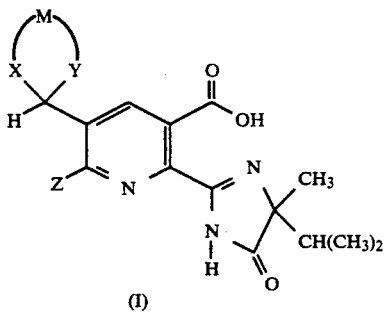

(I)

| X | Y | M | Z | mp °C. |
|---|---|---|---|---|
| O | O | CH=CHCH₂ | H | |
| O | O | (CH₃)=CHCH₂ | H | |
| O | O | CH=CHCH(CH₃) | H | |
| O | S | COCH₂ | H | |
| O | O | CH₂CH(CO₂CH₃) | H | |

EXAMPLE 30

Preparation of Sodium 5-(1,3-dioxolan-2-yl)-2-(4-isopropyl-4-methyl-5-oxo-2-imidazolin-2-yl)nicotinate

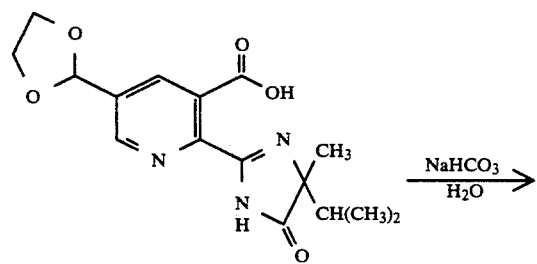

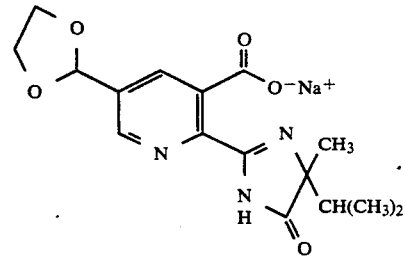

5-(1,3-Dioxolan-2-yl)-2-(4-isopropyl-4-methyl-5-oxo-2-imidazolin-2-yl)nicotinic acid (0.507 g, 0.00152 mol), sodium bicarbonate (0.12 g, 0.00143 mol), water and tetrahydrofuran is heated at reflux temperature for 1 hour. Concentration in vacuo yields a solid which is triturated with ether to give the title compound as an orange solid (0.39 g, 72%), mp 209°-210° C., identified by IR and NMR spectral analyses.

EXAMPLE 31

Preparation of 5-(1,3-Dioxolan-2-yl)-2-(4-isopropyl-4-methyl-5-oxo-2-imidazolin-2-yl)nicotinic acid, compound with diisopropylamine

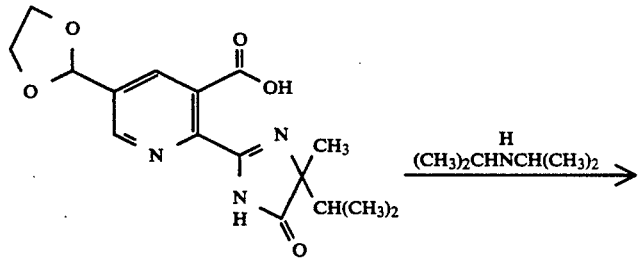

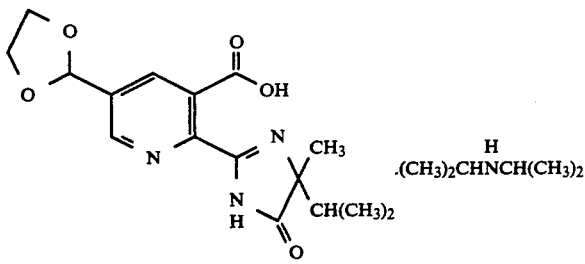

A solution of 5-(1,3-dioxolan-2-yl)-2-(4-isopropyl-4-methyl-5-oxo-2-imidazolin-2-yl)nicotinic acid (0.505 g, 0.00152 mol), diisopropylamine (0.23 g, 0.00163 mol) and tetrahydrofuran is heated for one hour and 30 minutes. Concentration in vacuo gives the title compound as a pale yellow solid (0.54 g, 82%), mp 102°–104° C., identified by IR and NMR spectral analyses.

EXAMPLE 32

Preparation of 7-(1,3-Dioxolan-2-yl)-3-isopropyl-3-methyl-5H-imidazo[1',2':1,2]pyrrolo[3,4-b]pyridine-2(3H), 5-dione

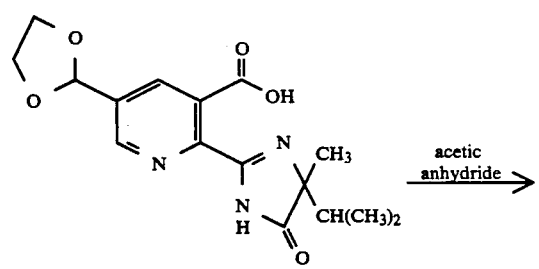

5-(1,3-Dioxolan-2-yl)-2-(4-isopropyl-4-methyl-5-oxo-2-imidaolin-2-yl)nicotinic acid (10.02 g, 0.03 mol) and acetic anhydride in toluene is heated at reflux temperature for 5 hours. Concentration in vacuo gives the title compound as an orange solid (11.10 g, 100%), mp 146°–148° C., identified by IR and NMR spectral analyses.

EXAMPLE 33

Preparation of 7-(1,3-Dioxolan-2-yl)-2-isopropyl-2-methyl-5H-imidazo[1',2':1,2]pyrrolo[3,4-b]pyridine-3(2H), 5-dione

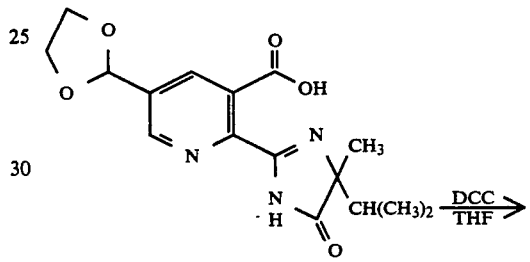

A solution of 5-(1,3-dioxolan-2-yl)-2-(4-isopropyl-4-methyl-5-oxo-2-imidazolin-2-yl)nicotinic acid (1.0 g, 0.003 mol) and dicyclohexylcarbodiimide (0.65 g, 0.003 mol) in tetrahydrofuran (5 mL) is stirred at reflux temperature for 1.5 hours. After cooling, the reaction mixture is filtered. The filtrate is concentrated in vacuo to afford the title compound (0.68 g, 72%) as a pale yellow solid, mp 102°–104° C., identified by IR and NMR spectral analyses.

EXAMPLE 34

Preparation of Methyl 2-(4-isopropyl-4-methyl-5-oxo-2-imidazolin-2-yl)-5-(1,3-dioxolan-2-yl)nicotinate

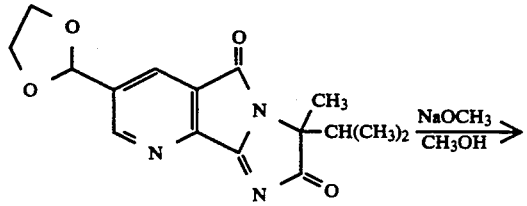

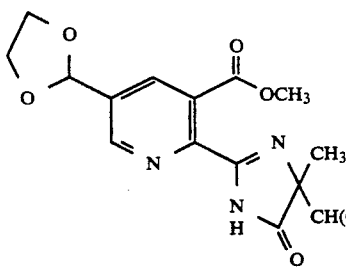

7-(1,3-Dioxolan-2-yl)-3-isopropyl-3-methyl-5H-imidazo[1',2':1,2]pyrrolo[3,4-b]pyridine-2(3H), 5-dione (4.05 g, 0.0128 mol) and sodium methoxide (0.73 g, 0.0135 mol) in methanol is heated at reflux temperature for 40 minutes then cooled to room temperature. The reaction mixture is quenched with 2 molar hydrochloric acid, poured into water and extracted with methylene chloride. The combined methylene chloride extracts are dried over anhydrous magnesium sulfate and concentrated in vacuo to give the title compound as an orange oil (3.88 g, 87%), identified by IR and NMR spectral analyses.

EXAMPLE 35

Preemergence herbicidal evaluation of test compounds

The preemergence herbicidal activity of the compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.016 to 8.0 kg per hectare of test compound per cup. The treated cups are then placed on greenhouse benches, watered and cared for in accordance with conventional greenhouse procedures. From four to five weeks after treatment, the tests are terminated and each cup is examined and rated according to the rating system set forth below. Data obtained are reported in Table I below. Where more than one test is involved for a given compound, the data are averaged.

Plant species employed in these evaluations are reported by header abbreviation, common name and scientific name.

Compounds employed in this preemergence herbicidal evaluation and in the post-emergence evaluation in the following example are given a compound number and identified by name. Data in Table I are reported by compound number.

Herbicide Rating Scale

Results of herbicide evaluation are expressed on a rating scale (0–9). The scale is based upon a visual observation of plant stand, vigor, malformation, size, chlorosis and overall plant appearance as compared with a control.

| Rating | Meaning | % Control Compared to Check |
|---|---|---|
| 9 | Complete Kill | 100 |
| 8 | Approaching Complete kill | 91–99 |
| 7 | Good Herbicidal Effect | 80–90 |
| 6 | Herbicidal Effect | 65–79 |
| 5 | Definite Injury | 45–64 |
| 4 | Injury | 30–44 |
| 3 | Moderate Effect | 16–29 |
| 2 | Slight Effect | 6–15 |
| 1 | Trace Effect | 1–5 |
| 0 | No Effect | 0 |

| PLANT SPECIES EMPLOYED IN HERBICIDAL EVALUATIONS | | |
|---|---|---|
| HEADER ABB | COMMON NAME | SCIENTIFIC NAME |
| BARNYARDGR | BARNYARDGRASS | *ECHINOCHLOA CRUS-GALLI*, (L)BEAU |
| FOXTAIL SP | FOXTAIL SPP. | *SETARIA* SPP. |
| P NUTSEDGE | NUTSEDGE, PURPLE | *CYPERUS RONTUNDUS*, L. |
| WILD OATS | OAT, WILD | *AVENA FATUA*, L. |
| QUACKGRASS | QUACKGRASS | *AGROPYRON REPENS*, (L)BEAUV |
| FLD BINDWD | BINDWEED, FIELD (RHIZOME) | *CONVOLVULUS ARVENSIS*, L. |
| MRNGLRY SP | MORNINGGLORY SPP. | *IPOMOEA* SPP. |
| WILD MUSTD | MUSTARD, WILD | *BRASSICA KABER*, (DC)L.C.WHEELR |
| RAGWEED | RAGWEED, COMMON | *AMBROSIA ARTEMISIIFOLIA*, L. |
| VELVETLEAF | VELVETLEAF | *ABUTILON THEOPHRASTI*, MEDIC. |
| SUGARBEETS | SUGARBEETS | *BETA VULGARIS*, L. |
| CORN FIELD, | CORN, FIELD | *ZEA MAYS*, L. |
| COTTON | COTTON | *GOSSYPIUM HIRSUTUM*, L. |
| SOYBEAN | SOYBEAN | *GLYCINE MAX* |

| COMPOUNDS EVALUATED AS HERBICIDAL AGENTS | |
|---|---|
| Compound No. | |
| 1 | 5-(1,3-dioxolan-2-yl)-2-(4-isopropyl-4-methyl-5-oxo-2-imidazolin-2-yl)nicotinic acid |
| 2 | 5-(5,5-dimethyl-1,3-dioxan-2-yl)-2-(4-isopropyl-4-methyl-5-oxo-2-imidazolin-2-yl)nicotinic acid |
| 3 | 5-(1,3-dioxan-2-yl)-2-(4-isopropyl-4-methyl-5-oxo-2-imidazolin-2-yl)nicotinic acid |
| 4 | 6-chloro-5-(1,3-dioxolan-2-yl)-2-(4-isopropyl-4-methyl-5-oxo-2-imidazolin-2-yl)nicotinic acid |
| 5 | 5-(1,3-dioxolan-2-yl)-2-(4-isopropyl-4-methyl-5-oxo-2-imidazolin-2-yl)-6-methoxynicotinic acid |
| 6 | 5-(1,2-dimethyl-3-diaziridinyl)-2-(4-isopropyl-4-methyl-5-oxo-2-imidazolin-2-yl)nicotinic acid |
| 7 | 5-(1,3-dioxolan-2-yl)-2-(4-isopropyl-4-methyl-5-oxo-2-imidazolin-2-yl)-6-methylnicotinic acid |
| 8 | 2-(4-isopropyl-4-methyl-5-oxo-2-imidazolin-2-yl)-5-(1,3-oxathiolan-2-yl)-nicotinic acid |
| 9 | 5-(1,3-dioxepan-2-yl)-2-(4-isopropyl-4-methyl-5-oxo-2-imidazolin-2-yl)nicotinic acid |
| 10 | 5-(1,3-dioxolan-2-yl)-2-(4-isopropyl-4-methyl-5-oxo-2-imidazolin-2-yl)nicotinic acid, compound with diisopropylamine |
| 11 | 5-(1,3-dioxolan-2-yl)-2-(4-isopropyl-4-methyl-5-oxo-2-imidazolin-2-yl)nicotinic acid, sodium salt |
| 12 | methyl 2-(4-isopropyl-4-methyl-5-oxo-2-imidazolin-2-yl)-5-(1,3-dioxolan-2-yl)-nicotinate |
| 13 | 2-(4-isopropyl-4-methyl-5-oxo-2-imidazolin-2-yl)-5-(3-methyl-2-oxazolidinyl)nicotinic acid, compound with 2-(methylamino)ethanol |

| | -continued |
|---|---|
| 14 | 2-(4-isopropyl-4-methyl-5-oxo-2-imidazolin-2-yl)-5-(4-methyl-1,3-dioxolan-2-yl)nicotinic acid |
| 15 | ammonium 5-(1-acetyl-3-methyl-2-imidazolidinyl)-2-(4-isopropyl-4-methyl-5-oxo-2-imidazolin-2-yl)nicotinate |
| 16 | 5-(3-acetyl-2-oxazolidinyl)-2-(4-isopropyl-4-methyl-5-oxo-2-imidazolin-2-yl)nicotinic acid |
| 17 | 5-(3-carboxy-2-oxazolidinyl)-2-(4-isopropyl-4-methyl-5-oxo-2-imidazolin-2-yl)nicotinic acid, 5-ethyl ester |
| 18 | 5-[3-(dimethylcarbamoyl)-2-oxazolidinyl]-2-(4-isopropyl-4-methyl-5-oxo-2-imidazolin-2-yl)nicotinic acid, 5-methyl ester |
| 19 | 5-(3-carboxy-2-oxazolidinyl)-2-(4-isopropyl-4-methyl-5-oxo-2-imidazolin-2-yl)nicotinic acid, 5-methyl ester |
| 20 | methyl 2-(4-isopropyl-4-methyl-5-oxo-2-imidazolin-2-yl)-5-(4-methyl-6-oxo-1,3-dioxan-2-yl)nicotinate |
| 21 | 5-(1,3-dithiolan-2-yl)-2-(4-isopropyl-4-methyl-5-oxo-2-imidazolin-2-yl)nicotinic acid |
| 22 | 7-(1,3-dioxolan-2-yl)-3-isopropyl-3-methyl-5$\underline{H}$-imidazo[1',2':1,2]pyrrolo[3,4-$\underline{b}$]pyridine-2(3$\underline{H}$), 5-dione |
| 23 | 7-(1,3-dioxolan-2-yl)-2-isopropyl-2-methyl-5$\underline{H}$-imidazo[1',2':1,2]pyrrolo[3,4-$\underline{b}$]pyridine-3(2$\underline{H}$), 5-dione |
| 24 | 5-(3-isobutyryl-2-oxazolidinyl)-2-(4-isopropyl-4-methyl-5-oxo-2-imidazolin-2-yl)nicotinic acid |
| 25 | ethyl 2-[5-carboxy-6-(4-isopropyl-4-methyl-5-oxo-2-imidazolin-2-yl)-3-pyridyl]tetrahydro-2$\underline{H}$-1,3-oxazine-3-carboxylate |

TABLE I

| PRE-EMERGENCE TESTS - RATES IN KG/HA | | | | | | | | |
|---|---|---|---|---|---|---|---|---|
| Compound No | RATE | BARNYARDGRA | FOXTAIL SP | P NUTSEDGE | WILD OATS | QUACK GRASS | FLD BINDWD | MRNGLRY SP |
| 1 | .500 | 8.0 | 9.0 | 9.0 | 9.0 | 9.0 | 9.0 | 8.0 |
| 2 | .500 | 0.0 | 2.0 | 9.0 | 4.0 | 8.0 | 8.0 | 2.0 |
| 3 | .500 | 8.0 | 9.0 | 9.0 | 9.0 | 9.0 | 9.0 | 9.0 |
| 4 | .500 | 0.0 | 7.0 | 9.0 | 9.0 | 7.0 | 2.0 | 7.0 |
| 5 | .500 | 0.0 | 0.0 | 9.0 | 6.0 | 6.0 | 9.0 | 7.0 |
| 6 | .500 | 2.0 | 8.0 | 2.0 | 9.0 | 7.0 | 7.0 | 2.0 |
| 7 | .500 | 2.0 | 7.0 | 9.0 | 8.0 | 9.0 | 9.0 | 7.0 |
| 8 | .500 | 6.0 | 8.0 | 9.0 | 3.0 | 7.0 | 9.0 | 8.0 |
| 9 | .500 | 8.0 | 8.0 | 2.0 | 9.0 | 9.0 | 9.0 | 9.0 |
| 10 | .500 | 9.0 | 9.0 | 9.0 | 9.0 | 9.0 | 9.0 | 9.0 |
| 11 | .500 | 9.0 | 9.0 | 9.0 | 9.0 | 9.0 | 9.0 | 9.0 |
| 12 | .500 | 9.0 | 9.0 | 8.0 | 9.0 | 9.0 | 9.0 | 8.0 |
| 13 | .500 | 4.0 | 9.0 | 6.0 | 9.0 | 9.0 | 9.0 | 8.0 |
| 14 | .500 | 8.0 | 9.0 | 9.0 | 9.0 | 9.0 | 9.0 | 9.0 |
| 15 | .500 | 0.0 | 0.0 | 0.0 | 0.0 | 0.0 | 0.0 | 0.0 |
| 16 | .500 | 0.0 | 0.0 | 0.0 | 0.0 | 0.0 | 0.0 | 0.0 |
| 17 | .500 | 0.0 | 4.0 | 0.0 | 7.0 | 7.0 | 9.0 | 0.0 |
| 18 | .500 | 0.0 | 0.0 | 0.0 | 0.0 | 0.0 | 0.0 | 0.0 |
| 19 | .500 | 0.0 | 0.0 | 0.0 | 7.0 | 2.0 | 7.0 | 0.0 |
| 20 | .500 | 0.0 | 0.0 | 0.0 | 0.0 | 0.0 | 0.0 | 0.0 |
| 21 | .500 | 0.0 | 0.0 | 0.0 | 0.0 | 0.0 | 0.0 | 0.0 |
| 22 | .500 | 6.0 | 9.0 | 8.0 | 9.0 | 9.0 | 9.0 | 8.0 |
| 23 | .500 | 8.0 | 9.0 | 9.0 | 8.0 | 9.0 | 9.0 | 9.0 |
| 24 | .500 | 0.0 | 0.0 | 0.0 | 0.0 | 0.0 | 0.0 | 0.0 |
| 25 | .500 | 0.0 | 0.0 | 0.0 | 7.0 | 2.0 | | 0.0 |

| Compound No | WILD MUSTD | RAGWEED | VELVETLEAF | SUGAR BEETS | CORN FIELD | COTTON | SOYBEAN WI |
|---|---|---|---|---|---|---|---|
| 1 | 9.0 | 7.0 | 9.0 | 9.0 | 9.0 | 9.0 | 5.0 |
| 2 | 7.0 | 0.0 | 6.0 | 9.0 | 7.0 | 4.0 | 0.0 |
| 3 | 9.0 | 8.0 | 9.0 | 9.0 | 9.0 | 9.0 | 4.0 |
| 4 | 8.0 | 4.0 | 8.0 | 9.0 | 7.0 | 6.0 | 2.0 |
| 5 | 8.0 | 0.0 | 4.0 | 9.0 | 7.0 | 4.0 | 2.0 |
| 6 | 7.0 | 0.0 | 6.0 | 4.0 | 9.0 | 6.0 | 0.0 |
| 7 | 6.0 | 4.0 | 6.0 | 9.0 | 9.0 | 7.0 | 0.0 |
| 8 | 9.0 | 2.0 | 7.0 | 9.0 | 6.0 | 6.0 | 2.0 |
| 9 | 9.0 | 9.0 | 9.0 | 9.0 | 9.0 | 8.0 | 3.0 |
| 10 | 9.0 | 8.0 | 8.0 | 9.0 | 9.0 | 9.0 | 4.0 |
| 11 | 9.0 | 8.0 | 8.0 | 9.0 | 9.0 | 9.0 | 3.0 |
| 12 | 9.0 | 8.0 | 8.0 | 9.0 | 9.0 | 9.0 | 3.0 |
| 13 | 9.0 | 4.0 | 9.0 | 9.0 | 9.0 | 8.0 | 5.0 |
| 14 | 9.0 | 9.0 | 8.0 | 9.0 | 9.0 | 8.0 | 7.0 |
| 15 | 0.0 | 0.0 | 0.0 | 0.0 | 0.0 | 0.0 | 0.0 |
| 16 | 0.0 | 0.0 | 0.0 | 0.0 | 0.0 | 0.0 | 0.0 |
| 17 | 9.0 | 0.0 | 3.0 | 6.0 | 7.0 | 1.0 | 0.0 |
| 18 | 0.0 | 0.0 | 0.0 | 0.0 | 0.0 | 0.0 | 0.0 |
| 19 | 9.0 | 0.0 | 0.0 | 2.0 | 2.0 | 0.0 | 0.0 |
| 20 | 0.0 | 0.0 | 0.0 | 0.0 | 0.0 | 0.0 | 0.0 |
| 21 | 4.0 | 0.0 | 4.0 | 3.0 | 0.0 | 0.0 | 0.0 |
| 22 | 8.0 | 7.0 | 7.0 | 9.0 | 9.0 | 8.0 | 2.0 |
| 23 | 9.0 | 8.0 | 7.0 | 9.0 | 9.0 | 9.0 | 4.0 |
| 24 | 0.0 | 0.0 | 0.0 | 0.0 | 0.0 | 0.0 | 0.0 |
| 25 | 8.0 | 0.0 | 0.0 | 8.0 | 0.0 | 0.0 | 0.0 |

EXAMPLE 36

Postemergence herbicidal evaluation of test compounds

The postemergence herbicidal activity of the compounds of the present invention is determined by the following tests, wherein a variety of monocotyledonous and dicotyledonous plants are treated with test compounds dispersed in aqueous acetone mixtures. In the tests, seedling plants are grown in jiffy flats for about two weeks. The test compounds are dispersed in 50/50 acetone/water mixtures containing 0.5% TWEEN® 20, a polyoxyethylene sorbitan monolaurate surfactant of Atlas Chemical Industries, in sufficient quantities to provide the equivalent of about 0.16 kg to 8.0 kg per hectare of active compound when applied to the plants through a spray nozzle operating at 40 psig for a predetermined time. After spraying, the plants are placed on greenhouse benches and are cared for in the usual manner, commensurate with conventional greenhouse practices. From four to five weeks after treatment, the seedling plants are examined and rated according to the rating system provided in Example 35 above. The data obtained are recorded in Table II below. The compounds evaluated are reported by compound number given in Example 35.

wherein $R_3$ is hydrogen; $R_1$ is $C_1$-$C_4$ alkyl;

$R_2$ is $C_1$-$C_4$ or $C_3$-$C_6$ cycloalkyl and when $R_1$ and $R_2$ are taken together with the carbon to which they are attached they may represent $C_3$-$C_6$ cycloalkyl;

X and Y are each independently oxygen, sulfur or $NR_4$;

M is $C_2$-$C_5$ alkylene optionally substituted with 1 or 2 $C_1$-$C_4$ alkyl groups, $C_1$-$C_4$ alkoxy, halogen, $CO_2R_6$ or oxo, and optionally interrupted by one oxygen or one sulfur, $C_2$ alkenylene optionally substituted with 1 or 2 $C_1$-$C_4$ alkyl groups or $CO_2R_6$, $C_3$ alkenylene optionally substituted with 1 or 2 $C_1$-$C_4$ alkyl groups, $CO_2R_6$ or oxo, methyleneamino, optionally substituted with $C_1$-$C_4$ alkyl or $CO_2R_6$, or a single bond, with the proviso that both X and Y are $NR_4$,

TABLE II

POST-EMERGENCE TESTS - RATES IN KG/HA

| Compound No | RATE | BARNYARDGRA | FOXTAIL SP | P NUTSEDGE | WILD OATS | QUACK GRASS | FLD BINDWD | MRNGLRY SP |
|---|---|---|---|---|---|---|---|---|
| 1 | .500 | 9.0 | 9.0 | 9.0 | 9.0 | 9.0 | 9.0 | 8.5 |
| 5 | .500 | 7.0 | 6.0 | 2.0 | 4.0 | 7.0 | 9.0 | 4.0 |
| 6 | .500 | 9.0 | 9.0 | 2.0 | 3.0 | 9.0 | 9.0 | 8.0 |
| 9 | .500 | 9.0 | 9.0 | 0.0 | 9.0 | 9.0 | 9.0 | 9.0 |
| 11 | .500 | 9.0 | 9.0 | 6.0 | 9.0 | 9.0 | 9.0 | 8.0 |
| 12 | .500 | 9.0 | 9.0 | 4.0 | 9.0 | 9.0 | 9.0 | 9.0 |
| 14 | .500 | 9.0 | 9.0 | 8.0 | 9.0 | 9.0 | 9.0 | 9.0 |
| 15 | .500 | 0.0 | 0.0 | 0.0 | 0.0 | 0.0 | 0.0 | 0.0 |
| 16 | .500 | 0.0 | 0.0 | 0.0 | 0.0 | 0.0 | 1.0 | 0.0 |
| 17 | .500 | 7.0 | 9.0 | 2.0 | 9.0 | 8.0 | 9.0 | 7.0 |
| 18 | .500 | 0.0 | 9.0 | 0.0 | 4.0 | 4.0 | 6.0 | 7.0 |
| 19 | .500 | 6.0 | 6.0 | 0.0 | 9.0 | 7.0 | 4.0 | 0.0 |
| 20 | .500 | 0.0 | 0.0 | 0.0 | 0.0 | 0.0 | 0.0 | 0.0 |
| 21 | .500 | 7.0 | 0.0 | 0.0 | 0.0 |  | 0.0 | 8.0 |
| 22 | .500 | 7.0 | 9.0 | 0.0 | 9.0 | 9.0 | 7.0 | 2.0 |
| 23 | .500 | 7.0 | 9.0 | 6.0 | 9.0 | 9.0 | 9.0 | 8.0 |
| 24 | .500 | 0.0 | 4.0 | 0.0 | 8.0 | 2.0 | 5.0 | 6.0 |
| 25 | .500 | 0.0 | 2.0 | 0.0 | 8.0 | 7.0 | 8.0 | 8.0 |

| Compound No | WILD MUSTD | RAGWEED | VELVETLEAF | SUGAR BEETS | CORN FIELD | COTTON | SOYBEAN WI |
|---|---|---|---|---|---|---|---|
| 1 | 9.0 | 8.0 | 9.0 | 9.0 | 9.0 | 8.0 | 7.0 |
| 5 |  | 4.0 | 4.0 | 8.0 | 9.0 | 3.0 | 2.0 |
| 6 | 9.0 | 2.0 | 8.0 | 9.0 | 9.0 | 9.0 | 2.0 |
| 9 | 9.0 | 9.0 | 9.0 | 9.0 | 9.0 | 8.0 | 5.0 |
| 11 | 9.0 | 9.0 | 9.0 | 9.0 | 9.0 | 9.0 | 4.0 |
| 12 | 9.0 | 6.0 | 8.0 | 9.0 | 9.0 | 8.0 | 1.0 |
| 14 | 9.0 | 7.0 | 9.0 | 9.0 | 9.0 | 9.0 | 4.0 |
| 15 | 2.0 | 0.0 | 0.0 | 2.0 | 0.0 | 0.0 | 0.0 |
| 16 | 9.0 | 0.0 | 1.0 | 8.0 | 0.0 | 4.0 | 0.0 |
| 17 | 9.0 | 2.0 | 5.0 | 9.0 | 9.0 | 8.0 | 8.0 |
| 18 | 9.0 | 0.0 | 2.0 | 9.0 | 6.0 | 4.0 | 0.0 |
| 19 | 9.0 | 2.0 | 3.0 | 8.0 | 9.0 | 7.0 | 6.0 |
| 20 | 0.0 | 0.0 | 0.0 | 0.0 | 0.0 | 0.0 | 0.0 |
| 21 | 0.0 | 0.0 |  | 8.0 | 2.0 | 4.0 | 0.0 |
| 22 | 9.0 | 2.0 | 6.0 | 9.0 | 9.0 | 4.0 | 0.0 |
| 23 | 9.0 | 8.0 | 9.0 | 9.0 | 9.0 | 7.0 | 2.0 |
| 24 | 8.0 | 0.0 | 7.0 | 8.0 | 7.0 | 7.0 | 0.0 |
| 25 | 9.0 | 0.0 | 5.0 | 9.0 | 8.0 | 7.0 | 3.0 |

What is claimed is:

1. A method for the preparation of a 5-hetrocyclic 2-(2-imidazolin-2-yl)pyridine compound having the formula I structure provided that the ring formed by M, X and Y and the carbon to which both X and Y are attached is no more than 8 atoms and provided that when the substituents on M are either alkoxy or halogen the substituted carbon is not bound to X or Y; and Z is hydrogen, halogen, $C_1$-$C_6$ alkoxy, or $C_1$-$C_6$ alkyl optionally substituted with $C_1$-$C_4$ alkoxy or halogen; which comprises reacting a compound having the structure

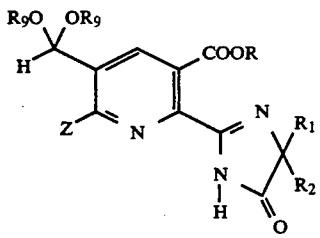

wherein $R_9$ is $C_1$-$C_4$ alkyl with at least two equivalents of hydrochloric acid in water to give the corresponding 5-formyl-2-(5-oxo-2-imidazolin-2-yl)nicotinic acid intermediate, reacting said intermediate with a compound having the structural formula

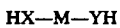

HX—M—YH wherein M, X and Y are as described above in the presence of an inert organic solvent at an elevated temperature to form a 5-heterocyclic 2-(2-imidazolin-2-yl-pyridine compound of formula I wherein $R_3$ is hydrogen.

2. A method for the preparation of a 5-heterocyclic 2-(2-imidazolin-2-yl)pyridine compound having the formula I structure

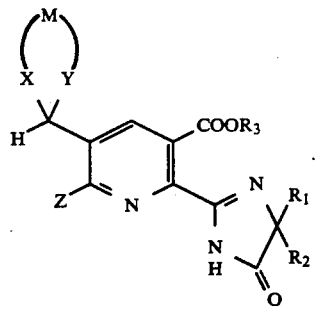

wherein $R_3$ is hydrogen and $R_1$, $R_2$, X M, Y and Z are as described in claim 1 which comprises reacting a compound having the structure

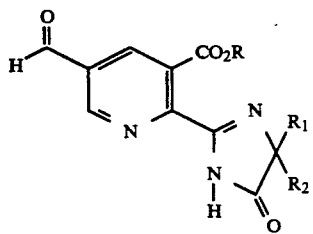

wherein $R_9$ is $C_1$-$C_4$ alkyl with a compound having the structural formula

HX—M—YH wherein M, X and Y are as described above in the presence of an inert organic solvent at an elevated temperature to form a 5-heterocyclic 2-(2-imidazolin-2-yl)-pyridine compound of formula I wherein $R_3$ is hydrogen.

* * * * *